United States Patent
Liu et al.

(10) Patent No.: US 9,910,012 B2
(45) Date of Patent: Mar. 6, 2018

(54) METHODS FOR REAL-TIME SAMPLING OF REACTION PRODUCTS

(71) Applicant: WAKO PURE CHEMICAL INDUSTRIES, LTD., Osaka-Shi, Osaka (JP)

(72) Inventors: Yu Liu, San Jose, CA (US); Chen Li, Santa Clara, CA (US)

(73) Assignee: Wake Pure Chemical Industries, Ltd., Osaka (JP)

(*) Notice: Subject to any disclaimer, the term of this patent is extended or adjusted under 35 U.S.C. 154(b) by 526 days.

(21) Appl. No.: 14/395,239

(22) PCT Filed: Apr. 18, 2013

(86) PCT No.: PCT/US2013/037197
§ 371 (c)(1),
(2) Date: Oct. 17, 2014

(87) PCT Pub. No.: WO2013/158898
PCT Pub. Date: Oct. 24, 2013

(65) Prior Publication Data
US 2015/0075983 A1    Mar. 19, 2015

Related U.S. Application Data

(60) Provisional application No. 61/635,295, filed on Apr. 19, 2012.

(51) Int. Cl.
*G01N 27/447* (2006.01)

(52) U.S. Cl.
CPC . *G01N 27/44791* (2013.01); *G01N 27/44743* (2013.01)

(58) Field of Classification Search
None
See application file for complete search history.

(56) References Cited

U.S. PATENT DOCUMENTS

| | | |
|---|---|---|
| 5,976,336 A | 11/1999 | Dubrow et al. |
| 8,394,324 B2 | 3/2013 | Bousse et al. |
| 2010/0173310 A1* | 7/2010 | Bousse ............ B01L 3/502746 435/6.11 |
| 2010/0200402 A1 | 8/2010 | Li et al. |

OTHER PUBLICATIONS

J. Dreier et al., Use of Bacteriophage MS2 as an Internal Control in Viral Reverse Transcription—PCR Assays, J. Clin. Microbiology, Sep. 2005, vol. 43(9), p. 4551-4557.

* cited by examiner

*Primary Examiner* — Samuel C Woolwine
(74) *Attorney, Agent, or Firm* — White & Case LLP

(57) ABSTRACT

Methods for analyzing reaction products from an assay chamber (11) in a microfluidic device comprise the steps of (I) moving a sample from the chamber (11) into a load channel (12), towards a separation channel (4), and (III) analyzing the sample present at an intersection (16) of the load channel (12) and the separation channel (4), by electrophoretic separation in the separation channel (4). During this separation, the step of (II) moving a next sample inside the load channel, towards a preload channel (13), is carried out.

14 Claims, 19 Drawing Sheets

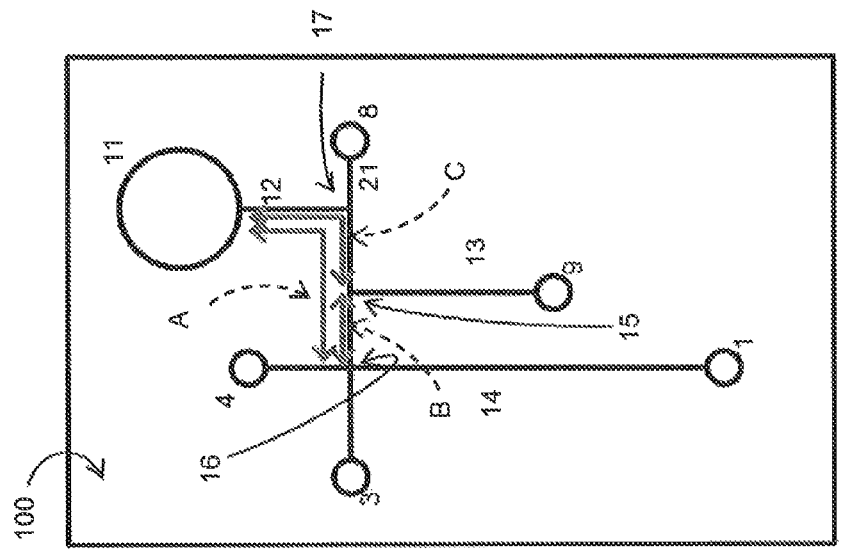

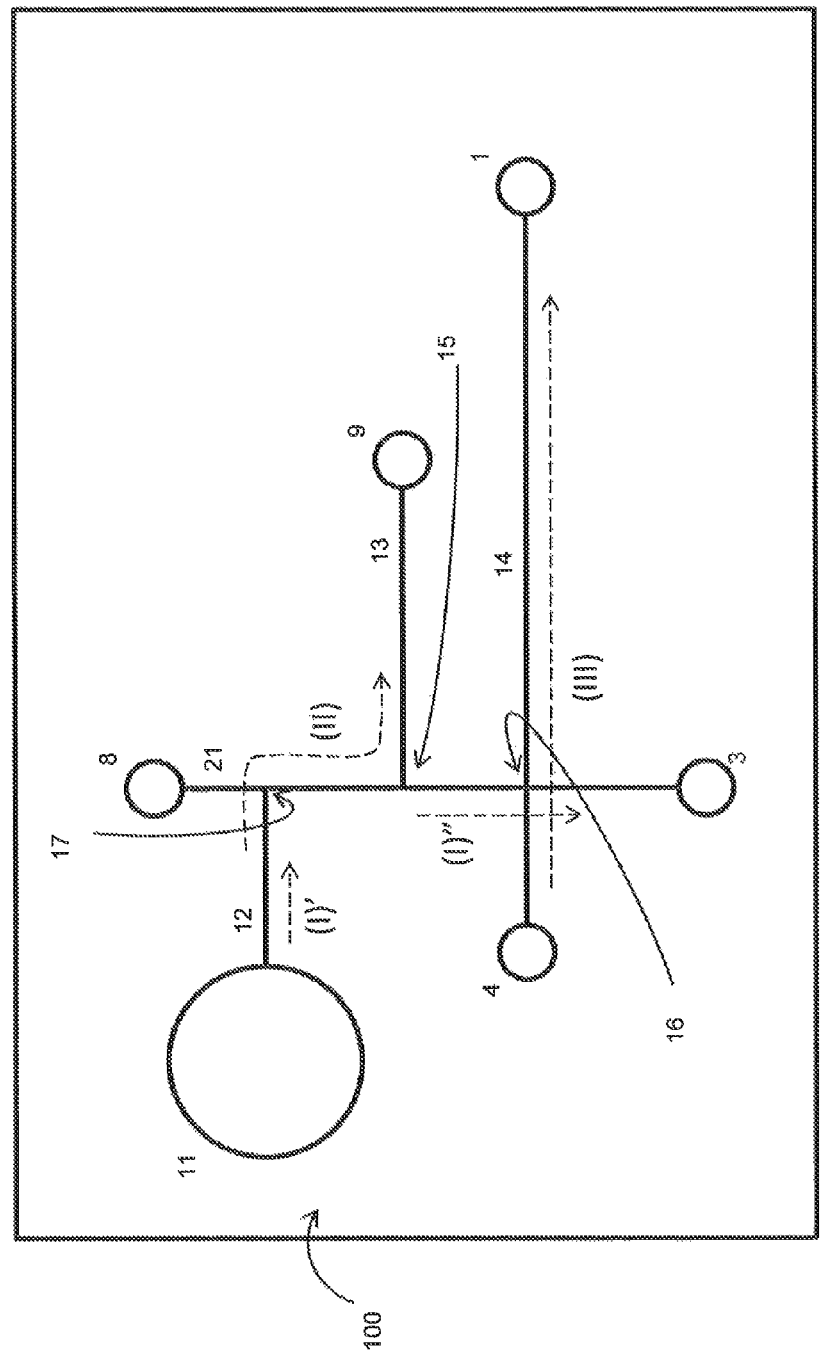

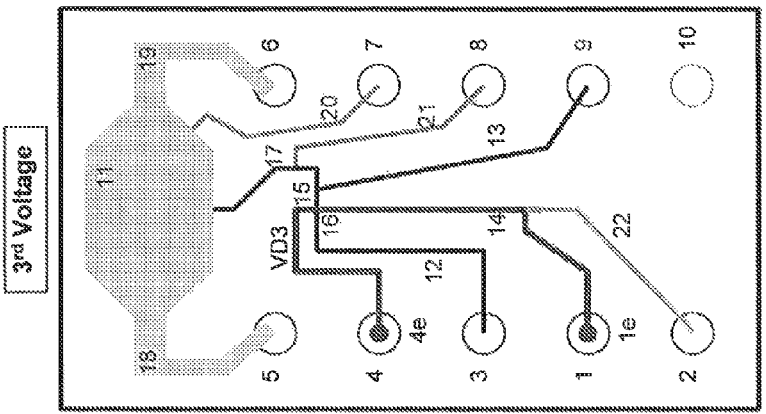
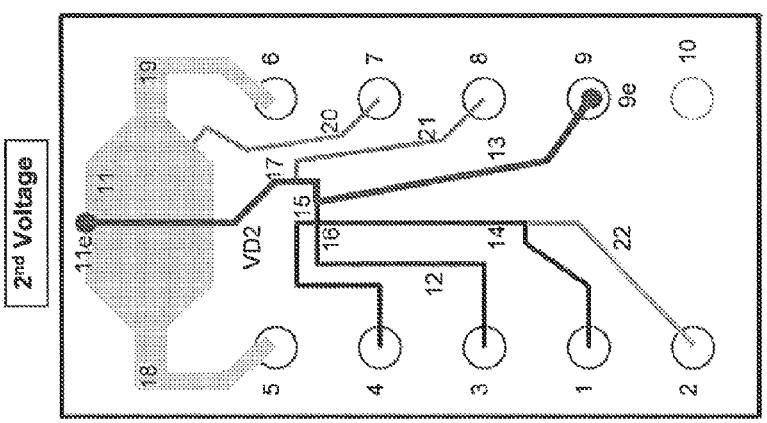
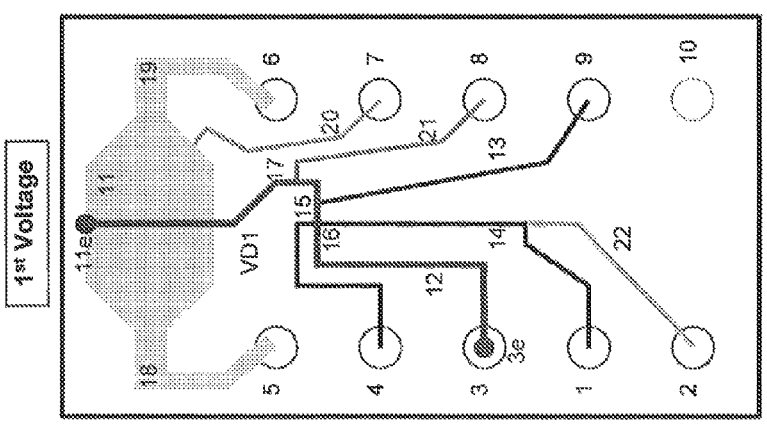

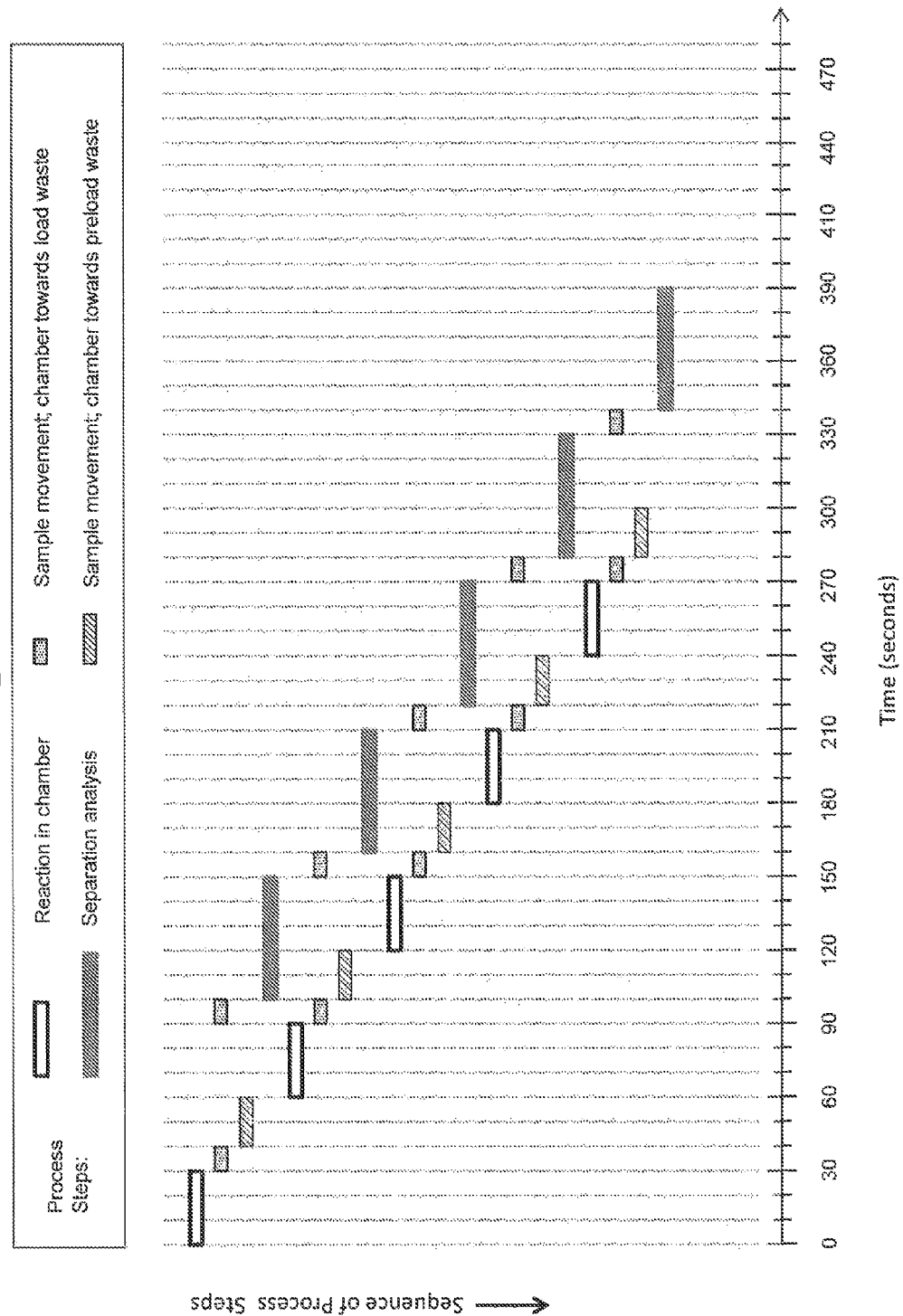

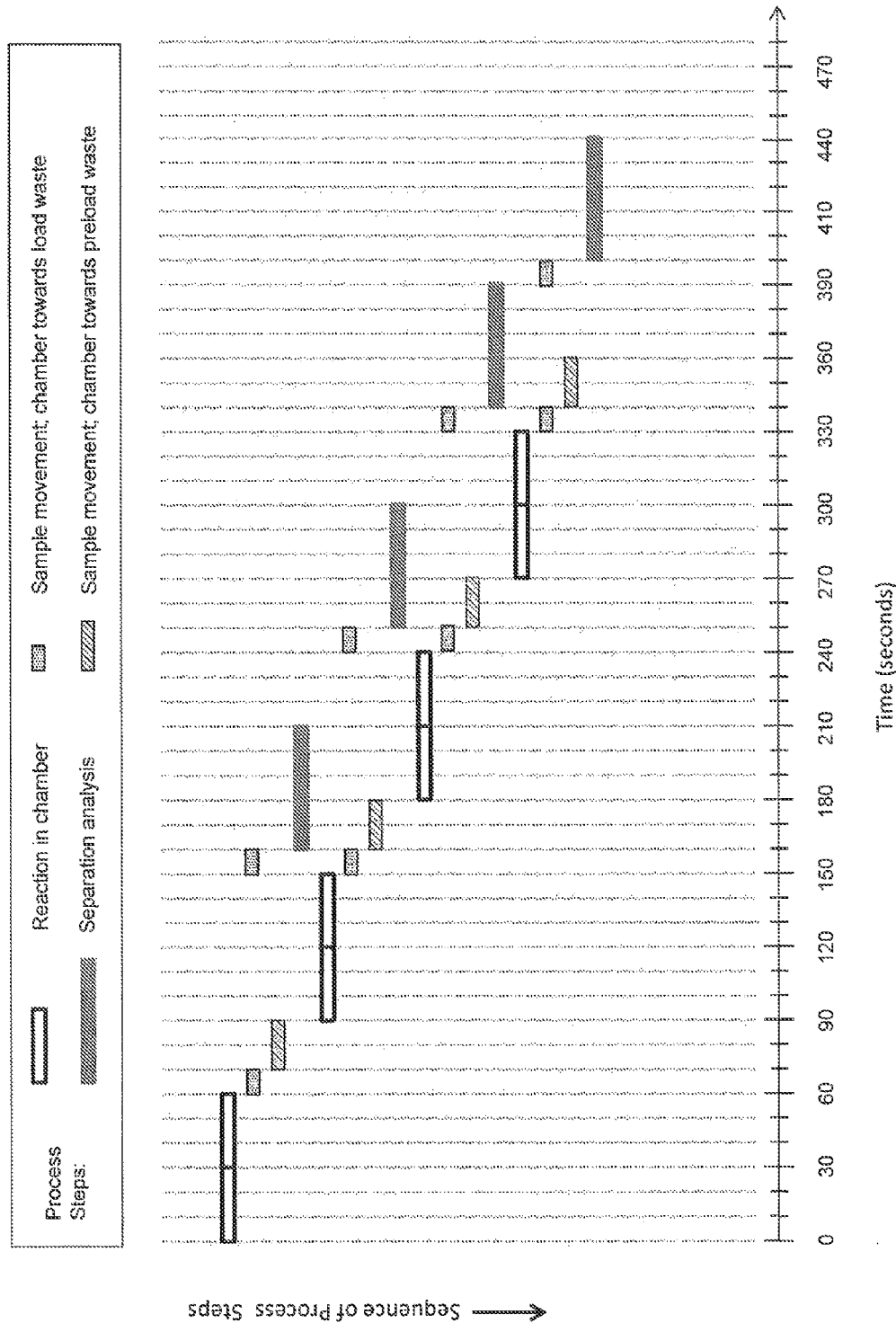

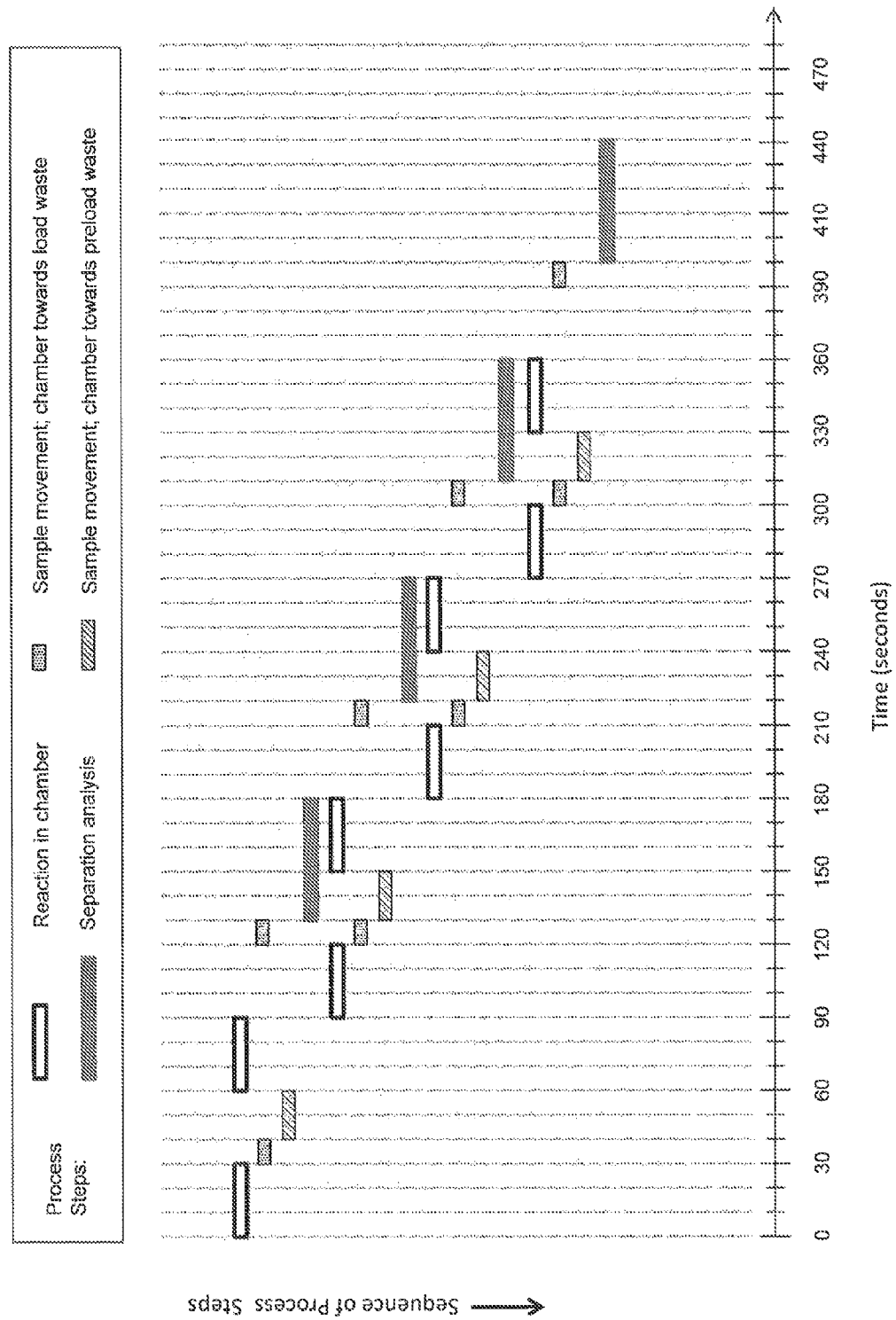

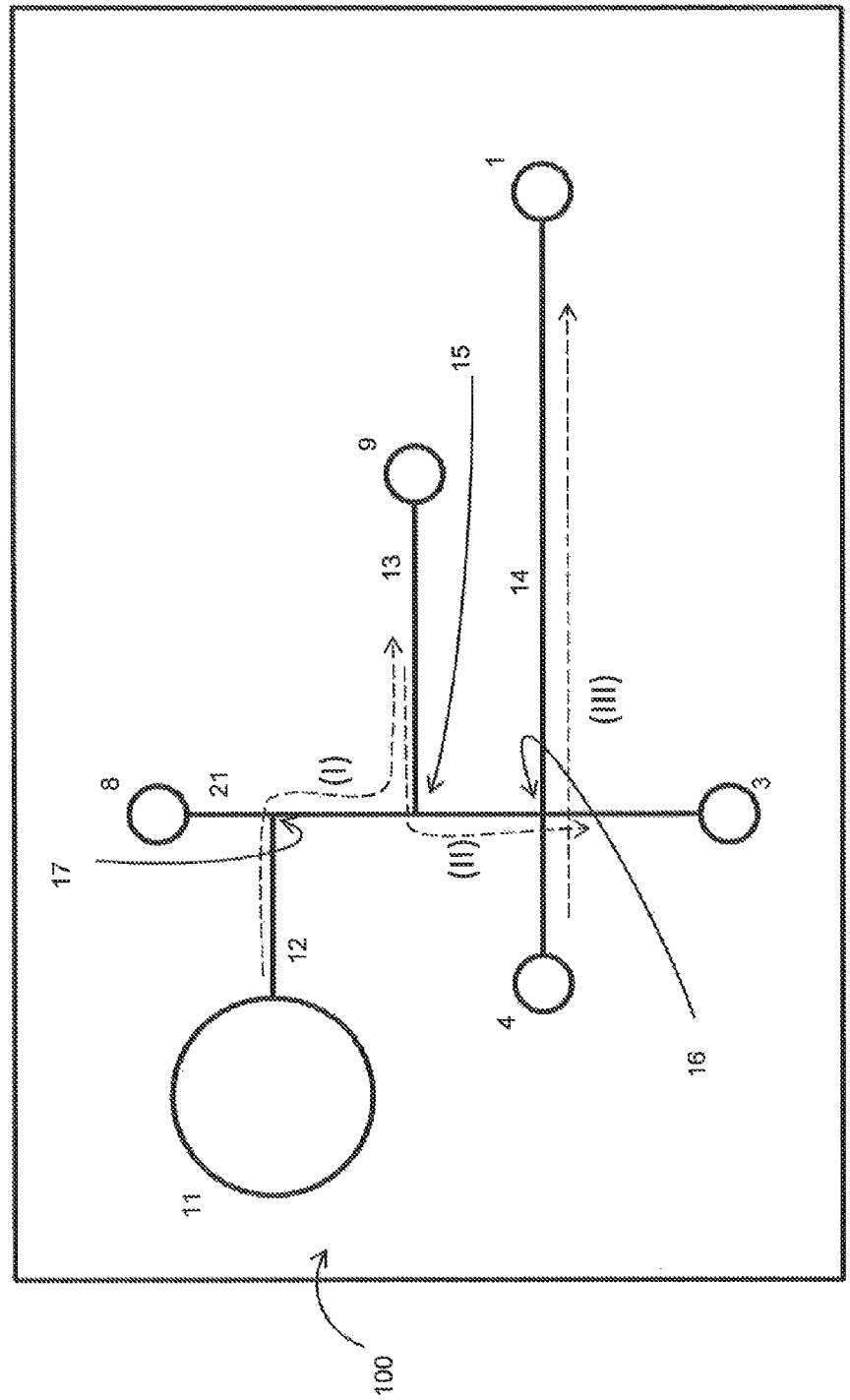

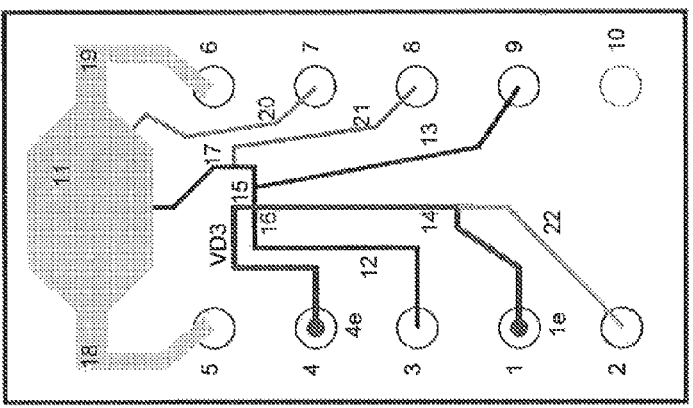
Fig. 6C 3rd Voltage
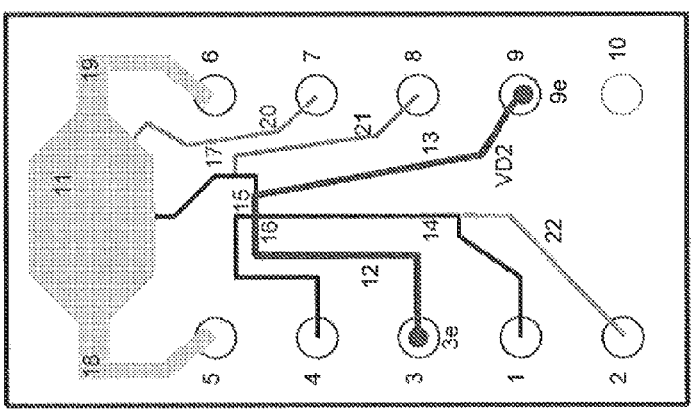
Fig. 6B 2nd Voltage
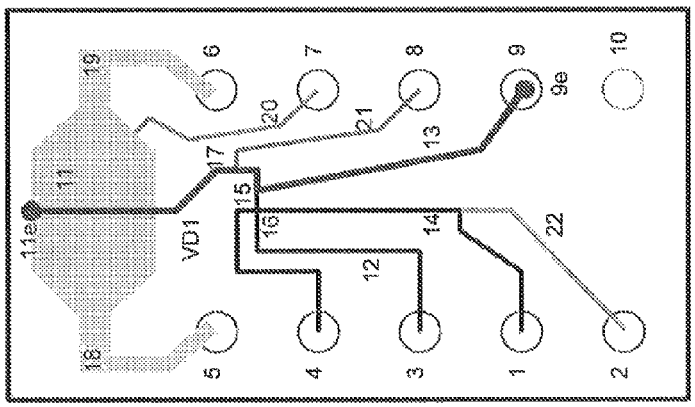
Fig. 6A 1st Voltage
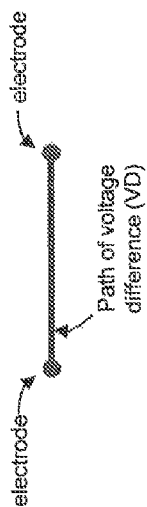

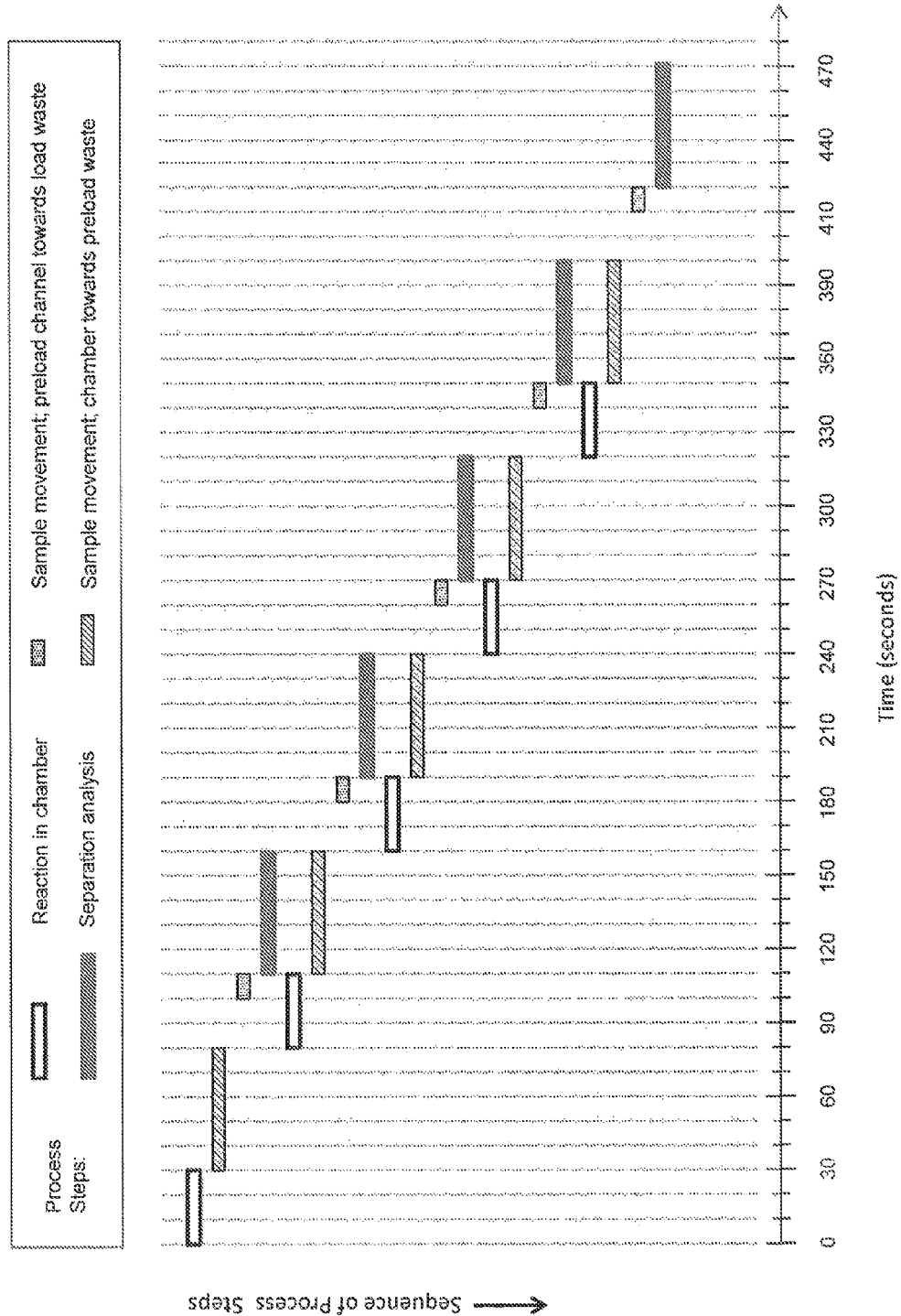

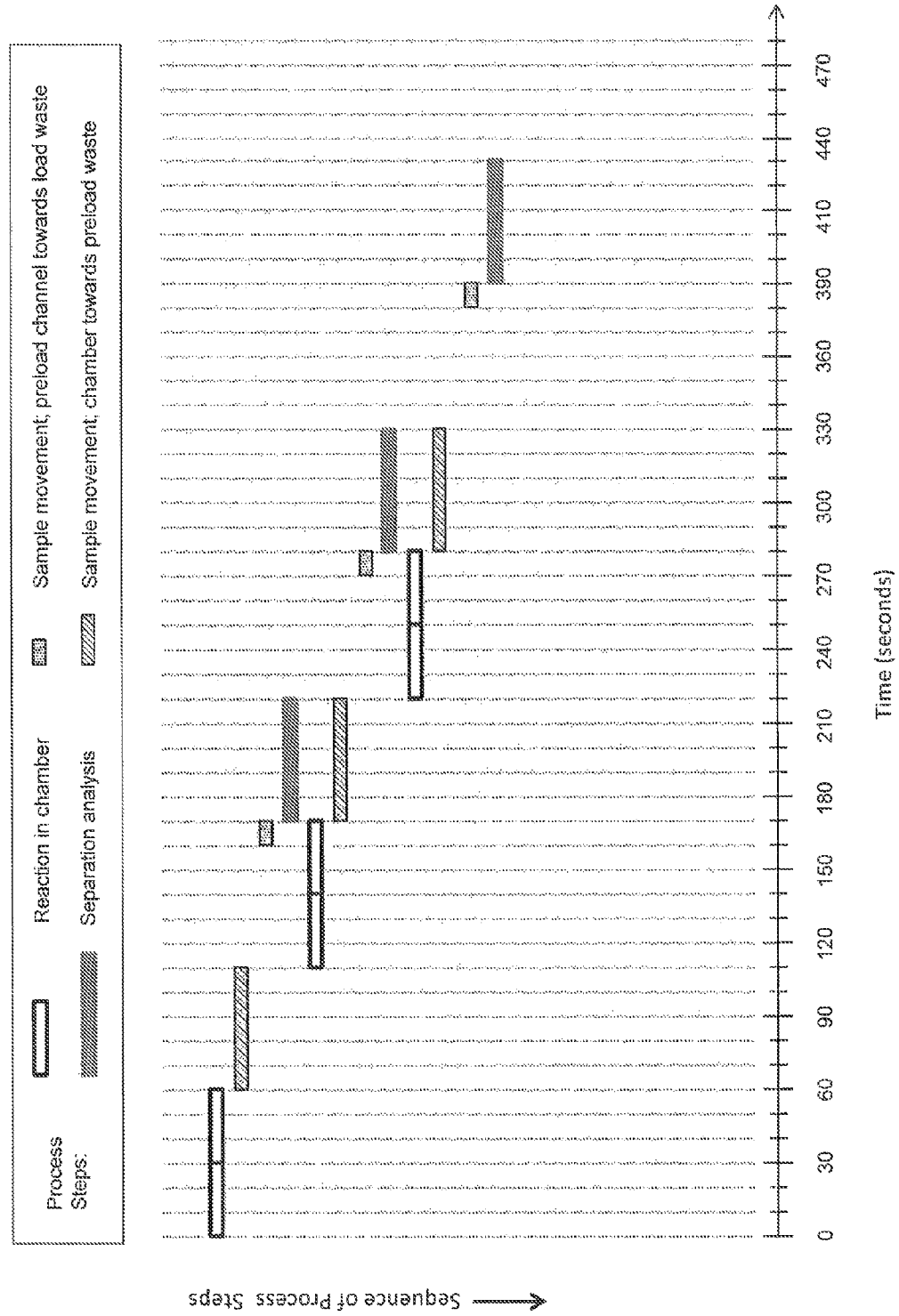

Fig. 9A

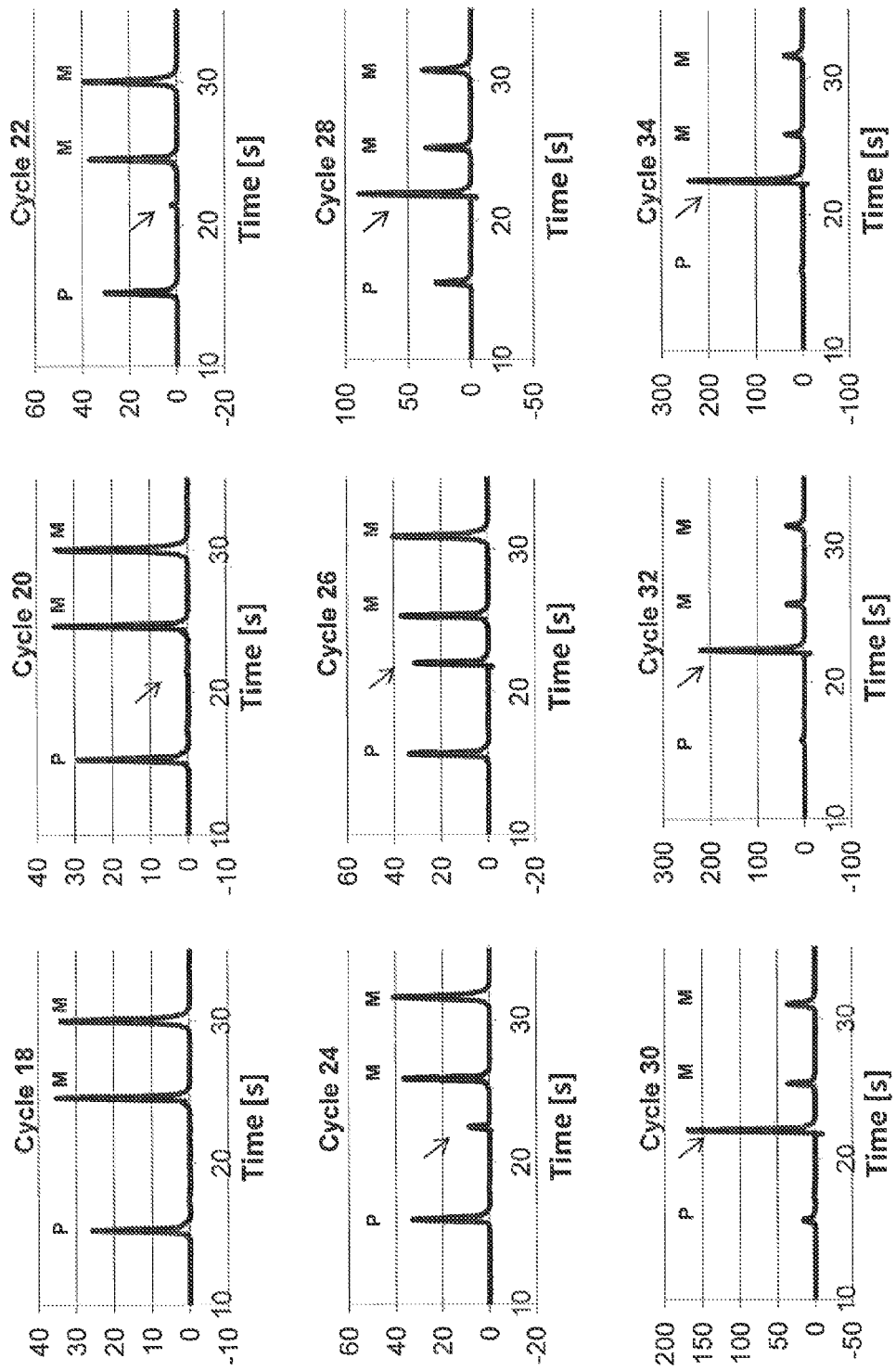

SEQUENCE LISTING

```
<160> NUMBER OF SEQ ID NOS: 8

<210> SEQ ID NO 1
<211> LENGTH: 28
<212> TYPE: DNA
<213> ORGANISM: Artificial Sequence
<220> FEATURE:
<223> OTHER INFORMATION: E. coli primer

<400> SEQUENCE: 1
atctatgact gtacgccact gtccctag                                          28

<210> SEQ ID NO 2
<211> LENGTH: 21
<212> TYPE: DNA
<213> ORGANISM: Artificial Sequence
<220> FEATURE:
<223> OTHER INFORMATION: E. coli primer

<400> SEQUENCE: 2
gcctagcaaa ctcggaagat t                                                 21

<210> SEQ ID NO 3
<211> LENGTH: 21
<212> TYPE: DNA
<213> ORGANISM: Artificial Sequence
<220> FEATURE:
<223> OTHER INFORMATION: HCV primer

<400> SEQUENCE: 3
gaaagcgtct agccatggcg t                                                 21

<210> SEQ ID NO 4
<211> LENGTH: 22
<212> TYPE: DNA
<213> ORGANISM: Artificial Sequence
<220> FEATURE:
<223> OTHER INFORMATION: HCV primer

<400> SEQUENCE: 4
ctcgcaagca ccctatcagg ca                                                22

<210> SEQ ID NO 5
<211> LENGTH: 21
<212> TYPE: DNA
<213> ORGANISM: Artificial Sequence
<220> FEATURE:
<223> OTHER INFORMATION: MS2 primer
```

-continued

```
<400> SEQUENCE: 5
ggtatagtgt gggaaaaggt g                                              21

<210> SEQ ID NO 6
<211> LENGTH: 21
<212> TYPE: DNA
<213> ORGANISM: Artificial Sequence
<220> FEATURE:
<223> OTHER INFORMATION: MS2 primer

<400> SEQUENCE: 6
acgagaacga actgagtaaa g                                              21

<210> SEQ ID NO 7
<211> LENGTH: 22
<212> TYPE: DNA
<213> ORGANISM: Artificial Sequence
<220> FEATURE:
<223> OTHER INFORMATION: Lambda phage primer

<400> SEQUENCE: 7
cgggataaca cgctcaccat ga                                             22

<210> SEQ ID NO 8
<211> LENGTH: 22
<212> TYPE: DNA
<213> ORGANISM: Artificial Sequence
<220> FEATURE:
<223> OTHER INFORMATION: Lambda phage primer

<400> SEQUENCE: 8
ggccagaccg agccttcaat ac                                             22
```

METHODS FOR REAL-TIME SAMPLING OF REACTION PRODUCTS

FIELD OF THE INVENTION

The invention relates to microfluidic devices configured to perform a reaction in a reaction chamber, move a sample of the reaction chamber contents to a separation channel, and analyze the sample in the separation channel, and methods of operating such devices.

BACKGROUND OF THE INVENTION

Microfluidic devices continue to be of great interest for conducting analyses of chemical and biological analytes. The terms "microfluidic" or "microscale" device generally refer to devices for manipulating fluids that comprise a network of microfluidic elements (e.g., channels and/or chambers), in which at least one element has at least one dimension in the range of from about 0.5 µm to about 500 µm. For example, channels may have a depth and/or a width in this range, while a chamber may have at least a depth in this range.

Microfluidic devices enable small-scale reactions, which provide numerous benefits, such as reduced reagent usage, reduced sample size, and rapid operation, as is well known in the art. In addition, the integration of several functions within a single device is possible, wherein a sample may be transported from one device element to another for subsequent handling, reaction, or analysis. This aspect of integration in turn further enables improvements in sample throughput because of reduced sample handling by operators or robotic stations, smaller space requirements, and even portability for remote or field usage.

Moreover, numerous sample wells, reaction chambers, and/or analysis regions can be provided on a single device, which in principle allows numerous analyses to be conducted in parallel. Bottlenecks may nonetheless arise if processes can only be conducted in sequence. For example, sample throughput is often limited by an analysis step, as one sample must wait for the analysis of a previous sample to conclude where the detector system (e.g., laser or optical detector) or analysis channel is shared. The microfluidic device layout of the microfluidic channels and wells is also a consideration, and the geometry of the device can be used to improve throughput by reducing transit times for analytes from one microfluidic element to another.

An example of improved device throughput based on channel geometry was disclosed by Dubrow et al. in U.S. Pat. No. 5,976,336. Dubrow et al. disclosed devices for electrophoretic separation analysis of different samples provided in multiple sample reservoirs. The devices have a single analysis channel, but sample reservoirs are located on each side of the analysis channel to maximize the number of reservoirs while minimizing the distance samples must travel to reach the analysis channel. Furthermore, while one sample introduced from a reservoir on one side of the separation channel is being analyzed by electrophoretic separation, a sample from a reservoir on the opposite side of the channel can be preloaded, that is, brought to a position in the load channel close to the separation channel. Once the analysis of the first sample is finished, the sample prepositioned in the load channel can complete its transit along the load channel from its sample reservoir to the intersection with the analysis channel and then be injected into the analysis channel for analysis.

Devices comprising functions and microfluidic elements other than just multiple sample reservoirs present different challenges and bottlenecks to high-throughput and/or reduced analysis time. In particular, microfluidic devices comprising reaction chambers present a challenge for coordinating sample movement within the device with the progress of the reaction. For example, for thermocycled reactions the temperature-induced changes to the sample and/or the transport properties caused by thermocycling must be considered and will limit when samples can be removed for analysis or other uses.

One application well-suited to a microfluidic device is an integrated device that performs a nucleic acid amplification reaction and analyzes the amplification products. For example, combining a chamber for an amplification reaction, such as PCR, with a separation channel for capillary electrophoresis (CE) detection provides a method for following the progress of the amplification in real time and quantifying the amount of target in the original sample.

Examples of such integrated devices are known in the art, including PCR-CE devices. One such device is disclosed in U.S. Pat. No. 8,394,324, by Bousse and Zhang, assigned to the same assignee, which is herein incorporated by reference in its entirety. A solution in a reaction chamber in the device is thermocycled to generate PCR amplification products, and after certain cycles, a sample of the reaction product is removed and analyzed for the amount of product generated in the amplification reaction. Generally, however, PCR-CE integrated devices pause the thermocycling process while the CE separation is conducted, or at least until the sample is transported from the chamber to the separation channel. This pause lengthens the total time needed to complete the analysis. Accordingly, there remains a need for devices and methods that are capable of more efficiently coordinating sample movement and completing an analysis in less time in order to increase sample throughput and decrease operating costs.

SUMMARY OF THE INVENTION

An integrated microfluidic device for the rapid analysis of samples is provided, as well as methods for operating the device. In particular, the device is configured for performing a reaction in a chamber, moving portions of the reaction product from the chamber from time to time, and analyzing the product. This device may be generally referred to as a reaction/analysis microfluidic device. Using the disclosed methods, the time to complete the reaction and periodic analysis of the generated products is significantly reduced compared to methods known in the art because the device structure enables, and the methods contemplate, conducting certain processes simultaneously rather than in series. Systems that incorporate the device and ancillary equipment for conducting the reaction and the detection processes are also disclosed.

In one embodiment, a microfluidic device is provided, the device comprising an reaction chamber, a load channel that leads from the reaction chamber to a load waste well, a separation channel that leads from a separation head well to a separation waste well and intersects the load channel, and a preload channel that leads from the load channel at a position between the reaction chamber and the load channel/separation channel intersection to a preload waste well.

A device may comprise more than one reaction chamber, and additional chambers may be connected to the same separation channel, either via the same load channel or a different load channel. Or, additional reaction chambers may be connected to a different separation channel. The capacity (number of reaction chambers and separation channels) and the layout of a device can be adjusted according to the application, the desired test throughput, manufacturing capabilities, peripheral instrumentation such as temperature controllers, detection apparatus, power supplies, and the like, that would be used as part of a system comprising the device.

In another embodiment, a microfluidic device further comprises a side channel leading from the load channel to a side head well, wherein the load channel/side channel junction is between the reaction chamber and the load channel/preload channel junction.

In another embodiment, a microfluidic device further comprises a focusing dye channel leading from the separation channel to a focusing dye well, wherein the separation channel/focusing dye channel junction is downstream of the detection point in the separation channel.

In further embodiments, a microfluidic device further comprises electrodes positioned in the chamber or in a well in electrochemical as well as fluidic communication with the contents of the chamber, the load waste well, the preload waste well, the separation head well, the separation waste well, and, if present, the focusing dye well and the side head well. Preferably, the electrodes are independently controllable. With independent control over the voltage (potential) applied to an electrode or the current flowing through an electrode, sample components can be electrokinetically moved between specific locations in the device. The electrodes are positioned such that they can make electrical contact with solution in each chamber or well, that is, solution in the chamber, or solution in the load waste well, and so forth.

The reaction chamber connects to at least two access channels and at least one load channel. Each access channel leads from the chamber to a separate access well. A fluid, for example, a reaction solution, is added to the reaction chamber using the access channels. Generally, the fluid is introduced into a first access well, moves via the first access channel into the chamber, and ultimately fills the chamber. The displaced air exits through the second access channel and second access well. Accordingly, the at least two access channels connect to the chamber so that the fluid may flow from one access channel into the chamber, fill the chamber, and exit through the second access channel. In one embodiment, the access channels connect to the chamber on opposite sides of the chamber.

The reaction chamber also connects to the load channel, as noted above. The load channel is part of the analysis channel network. The analysis channel network comprises the load channel, preload channel, and separation channel, and, if present, side channel.

The dimensions of channels in the analysis channel network are designed so as to enable the coordinated movement of small amounts of material through the device. The design is based on several considerations. One consideration relates to the size and/or the flow resistance of the analysis channel network in relation to the reaction chamber. As described in U.S. Pat. No. 8,394,324, this channel network may be configured to have a smaller internal volume than the reaction chamber in order that only a small fraction of the components in the reaction chamber need to be removed for analysis or other uses in the channel network. For example, the combined volume of the channels in the channel network can be about 100 times smaller, or about 100 times to about 1000 times smaller, or from about 300 times to about 1000 times smaller than the volume of the reaction chamber. Also as described in U.S. Pat. No. 8,394,324, the device may be designed to comprise an analysis channel network wherein the channels have small cross-sectional area, such that the hydrodynamic flow resistance of the channel network is higher than that of the reaction chamber. For example, sizing the channel dimensions such that the flow resistance ratio between the analysis channel network and the reaction chamber is about $10^3$ or more, or about $10^3$ to about $10^9$, or about $10^3$ to about $10^7$, or about $10^4$ to about $10^6$, provides a gate function at the entrance to the load channel from the reaction chamber. The design considerations and exemplary channel dimensions that can be used to achieve such values of hydrodynamic flow resistance are provided in U.S. Pat. No. 8,394,324.

A second consideration relates to the length along the load channel between the junctions and intersections with other channels and the length of the preload channel. By providing a device that meets the design criteria described herein for the lengths of the specified channel portions, the device can be used in methods that allow for coordinated sample movement within the analysis channel network and faster analysis of a series of samples. A discussion of the design criteria for the length of the load channel segments, and the typical ranges for such segments is provided below.

A system is also provided that comprises a reaction/analysis microfluidic device, and ancillary equipment used to perform the methods of the invention. Ancillary equipment may comprise a thermocycler device, a power supply for controlling the potential and/or current at the set of electrodes using with the microfluidic device, and a detection apparatus.

In one embodiment of the system, the thermocycler device contacts the microfluidic device in the region of the reaction chamber and is operated to control the temperature of the fluid in the reaction chamber. The thermocycler device may be capable of either or both heating or cooling. The thermocycler device can be used to incubate the fluid at a fixed temperature or the temperature can be varied as a function of time. In one embodiment, the temperature of the fluid in the reaction chamber is repeatedly raised and lowered using the thermocycler device such that PCR occurs when the necessary reagents, primers, and target are present. Other amplification reactions, such as ligase chain reaction (LCR), strand displacement amplification (SDA), nucleic acid sequence based amplification (NASBA), loop-mediated isothermal amplification (LAMP), rolling circle amplification (RCA), self-sustained sequence amplification (SSSR), transcription mediated amplification (TMA), and similar and related nucleic acid detection techniques can also be implemented using the methods and systems described herein, as one of skill in the art would readily understand. Enzymatic reactions can also be analyzed using the methods and systems.

In one embodiment of the system, the detection apparatus comprises equipment for performing laser-induced fluorescence detection of the contents of the separation channel. For example, a laser, optics, and a detector are aligned for inducing and detecting fluorescence from components within the separation channel. The alignment of the detection subsystem with the separation channel can be accomplished in numerous ways. For example, the microfluidic device can be manufactured with the detection region of the separation channel at a known location relative to a datum surface(s) for alignment within an apparatus. Or, a component of the detection system, such as the light source (e.g., laser) could be scanned over the microfluidic device to detect the separation channel and concomitantly its detection region by various techniques known in the art. Examples include providing a fluorescent marker substance in the separation channel and locating the detection region by detecting the fluorescent marker substance. A separation medium, such as a gel, housed in the channel may include a fluorescent marker substance, or, a fluorescent substance can be temporarily moved into the detection region (e.g., by electrophoresis) from a side channel in communication with the separation channel for the purpose of locating the channel before the start of the analysis. Numerous variations of a detection apparatus are possible and well-known to those of skill in the art. Variations include the wavelength of light, light beam shape, use of one or more wavelengths in the detection, as well as the type of light source and detector. The sensitivity required for a particular application is a factor in choosing the type of detection apparatus.

Methods for analyzing an assay sample which contains a nucleic acid such as DNA, RNA, and the like, such as a clinical sample, and the sample components that are formed therein in the course of an assay, in a microfluidic device are also provided. The methods use devices as described above.

One method comprises the steps of (a) adding an assay solution to the chamber, (b) applying a first voltage across the separation head well and separation waste well for a first length of time to inject into the separation channel a first set of sample components from the assay solution at a first time previously moved into a load channel/separation channel intersection region and to perform an analysis of the first set of sample components in the separation channel, (c) applying a second voltage across the chamber and the preload waste well for a second length of time to move a second set of sample components from the assay solution at a second time from the chamber into the preload channel via the load channel, (d) subsequent to step (b), applying a third voltage across the preload waste well and the load waste well for a third length of time to move the second set of sample components from the preload channel into the load channel and into the load channel/separation channel intersection region.

For example, in the above embodiment and for the analysis of ~100-500 base pair DNA fragments, a first voltage of 500-3000 V may be applied for 20-120 seconds, a second voltage of 300-1000 V may be applied for 20-60 seconds, and a third voltage of 400-1600 V may be applied for 10-40 seconds. These parameters are a guide to the order of magnitude of voltages and times that may be useful; design criteria for the operation of the method are provided below.

The method may further comprise performing a nucleic acid amplification reaction in the chamber. The method may yet further comprise repeating at least twice the series of steps: step (b), step (c), step (d), and (e) performing at least one amplification cycle beginning at the end of step (c), wherein optionally, the first time the series of steps is performed, step (b) is omitted, the subsequent series of steps begins after step (d) and step (e) ends, and, optionally, the last time the series of steps is repeated, the series of steps only includes step (b). The method may additionally comprise the above methods wherein step (b) and step (c) begin at about the same time, and one amplification cycle is performed in each step (e), which begins at the end of each step (c).

One method comprises the steps of (a) adding an assay solution to the chamber, (b) moving a first set of sample components from the assay solution in the chamber into the preload channel via the load channel, for a first length of time, such that the slowest moving sample component enters the preload channel, (c) moving the portion of the first set of sample components in the preload channel from the preload channel towards the load waste well and into a load channel/separation channel intersection region, for a second length of time, such that the slowest moving sample component reaches the load channel/separation channel intersection region, (d) injecting the first set of sample components from the load channel/separation channel intersection region into the separation channel; and (e) analyzing the first set of sample components in the separation channel. The method may further comprise: (f) at about the time of beginning step (e), moving a second set of sample components from the assay solution in the chamber into the preload channel via the load channel, for the first length of time, wherein the slowest moving component of the second set of sample components enters the preload channel.

One method comprises performing a nucleic acid amplification reaction in the microfluidic device and analyzing the amount of product generated at least once by electrophoretic separation in a separation channel in the same microfluidic device. The method comprises the steps of: (a) performing at least one amplification cycle in the amplification chamber to generate amplicons, (b) moving by electrophoresis amplicons from the amplification chamber into the preload channel via the load channel, (c) performing at least one amplification cycle to generate additional amplicons, (d) moving by electrophoresis amplicons from the preload channel towards the load waste well and into a load channel/separation channel intersection region, (e) performing the following cycle of steps at least twice: (1) moving by electrophoresis amplicons generated by the current amplification cycle from the reaction chamber into the preload channel via the load channel, (2) injecting the amplicons from the previous amplification cycle that are in the load channel/separation channel intersection region into the separation channel, (3) separating the injected amplicons along the separation channel by electrophoresis, (4) detecting the separated amplicons, (5) optionally, subsequent to step (e) (1) and at least partially overlapping in time with step (e)(6), performing at least one amplification cycle in the amplification chamber; and (6) moving by electrophoresis amplicons from the preload channel towards the load waste well and into the load channel/separation channel intersection region, wherein the progress of the nucleic amplification reaction is analyzed by detecting the amplicons generated as a function of the number of amplification cycles.

One method comprises the steps of (a) adding an assay solution to the chamber, (b) applying a first voltage across the chamber and the load waste well for a first length of time to move (i) a first set of sample components removed from the assay solution at a first time and previously moved into the load channel into a load channel/separation channel intersection region and (ii) a second set of sample components from the assay solution at a second time from the chamber into the load channel, (c) subsequent to step (b), applying a second voltage across the chamber and the preload waste well for a second length of time to continue to move the second set of sample components from the assay solution at a second time from the chamber and in the load channel towards the preload waste well, and (d) subsequent to step (b), applying a third voltage across the separation head well and separation waste well for a third length of time to inject the first set of sample components from the load channel/separation channel intersection region into the separation channel and to perform an analysis of the first set of sample components in the separation channel.

For example, in the above embodiment and for the analysis of ~100-500 base pair DNA fragments, a first voltage of 500-1500 V may be applied for 5-50 seconds, a second voltage of 300-1000 V may be applied for 20-60 seconds, and a third voltage of 500-3000 V may be applied for 20-120 seconds. These parameters are a guide to the order of magnitude of voltages and times that may be useful; design criteria for the operation of the method are provided below.

The method may further comprise performing a nucleic acid amplification reaction in the chamber. The method may yet further comprise repeating at least twice the series of steps: step (b), step (c), step (d), and (e) performing at least one amplification cycle beginning at the end of step (c), wherein optionally, the first time the series of steps is performed, step (d) is omitted, the subsequent series of steps begins after step (d) and step (e) ends, and, optionally, the last time the series of steps is repeated, the series of steps only includes step (b) and step (d). The method may additionally comprise the above methods wherein step (c) and step (d) begin when each step (b) ends, and one amplification cycle is performed in each step (e), which begins at the end of each step (c).

One method comprises the steps of (a) adding an assay solution to the chamber, (b) moving a first portion of a first set of sample components from the assay solution in the chamber into the load channel, for a first length of time, such that the fastest moving sample component does not reach the load channel/separation channel intersection region, (c) moving a second portion of the first set of sample components from the assay solution in the chamber as well as the first portion in the load channel towards the preload waste well, for a second length of time, (d) moving the first set of sample components in the load channel along the load channel and into a load channel/separation channel intersection region, for a third length of time, wherein the third length of time is the same as the first length of time, such that: (i) the distance moved by the slowest moving component during the third length of time is greater than the distance from the load channel/preload channel junction to the load channel/separation channel intersection, and (ii) the distance moved by the slowest moving component during the sum of the first, second, and third lengths of time is greater than the distance along the load channel from the chamber to the load channel/separation channel intersection, (e) injecting the first set of sample components from the load channel/separation channel intersection region into the separation channel, and (f) analyzing the first set of sample components in the separation channel.

The method may further comprise during step (b), moving a second set of sample components from the assay solution previously moved into the load channel into the load channel/separation channel intersection region, wherein the slowest moving sample component of the second set of sample components reaches the load channel/separation channel intersection region, and further comprising: (g) subsequent to step (b), injecting the second set of sample components from the load channel/separation channel intersection region into the separation channel and analyzing the second sample in the separation channel.

The method may yet further comprise during step (d), moving a first portion of a third set of sample components from the assay solution in the chamber into the load channel, wherein the fastest moving component of the third set of sample components does not reach the load channel/separation channel intersection region, further comprising: (h) during step (f), moving a second portion of the third set of sample components from the assay solution in the chamber into the load channel as well as the first portion in the load channel towards the preload waste well during a fourth length of time, wherein the fourth length of time is the same as the second length of time.

One method comprises the steps of (a) performing at least one amplification cycle in the amplification chamber to generate amplicons, (b) moving by electrophoresis a first portion of amplicons from the amplification chamber into and along the load channel towards the load waste well, such that the amplicons move a portion of the way along the load channel but do not reach the load channel/separation channel intersection, (c) moving by electrophoresis a second portion of amplicons from the amplification chamber into and, with the first portion of amplicons, along the load channel and towards the preload waste well, (d) performing one amplification cycle in the amplification chamber, and (e) performing the following cycle of steps at least twice: (1) moving by electrophoresis (i) a first portion of amplicons generated by the current amplification cycle, from the amplification chamber into and along the load channel towards the load waste well, such that the amplicons generated by the current amplification cycle move a portion of the way along the load channel but do not reach the load channel/separation channel intersection and (ii) amplicons previously moved into the load channel and towards the preload waste well following the previous amplification cycle, along the load channel and into a load channel/separation channel intersection region, (2) moving by electrophoresis a second portion of amplicons generated by the current amplification cycle, from the amplification chamber into and, with the first portion of amplicons in the load channel generated by the current amplification cycle, along the load channel and towards the preload waste well, (3) injecting the amplicons from the load channel/separation channel intersection region into the separation channel, (4) separating the injected amplicons along the separation channel by electrophoresis, (5) detecting the separated amplicons, and (6) optionally, subsequent to step (e)(2) and during steps (e)(3)-(5), performing at least one amplification cycle in the amplification chamber, wherein the progress of the nucleic amplification reaction is analyzed by detecting the amplicons generated as a function of the number of amplification cycles.

These and other objects and features of the invention will become more fully apparent when the following detailed description of the invention is read in conjunction with the accompanying drawings.

BRIEF DESCRIPTION OF THE DRAWINGS

FIG. 1A shows a microfluidic device according to one embodiment of the invention.

FIG. 1B shows a microfluidic device according to one embodiment of the invention.

FIG. 2 shows a movement pattern of sample components according to one embodiment of the invention.

FIGS. 3A, 3B, and 3C show a sequence of steps according to one embodiment of the invention.

FIGS. 4A, 4B, and 4C show exemplary time sequences of events according to embodiments of the invention.

FIG. 5 shows a movement pattern of sample components according to one embodiment of the invention.

FIGS. 6A, 6B, and 6C show a sequence of steps according to one embodiment of the invention.

FIGS. 7A and 7B show exemplary time sequences of events according to embodiments of the invention.

FIGS. 9A and 9B show the results of a real-time PCR-CE analysis conducted according to one embodiment of the invention described in Example 1.

FIGS. 11A and 11B show the results of a real-time PCR-CE analysis conducted according to one embodiment of the invention described in Example 3.

DETAILED DESCRIPTION

Figure 1C:
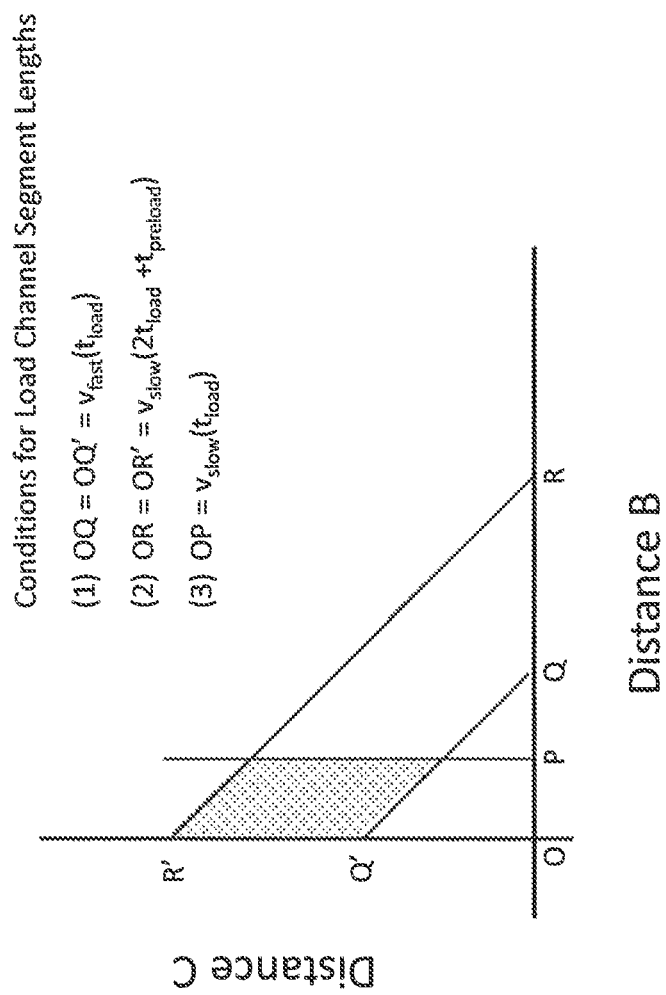
FIG. 1C shows a graphical solution to design parameters for a microfluidic device according to one embodiment of the invention.

The devices, methods, and systems of the invention generally are useful for conducting a reaction and analyzing the reaction products within a single microfluidic device. The reactions may involve molecular biological or chemical reactions or assays. The reaction conditions may include incubating or thermocycling the reaction solution. Reaction products are withdrawn periodically or from time to time from the reaction chamber and transported via a channel network to a separation channel for analysis. One particular application is for real-time PCR analysis or quantitative PCR (qPCR). In such an application, an oligonucleotide primer pair is contacted with a sample of interest in a solution that contains the necessary reagents for a PCR reaction, such as a polymerase enzyme and nucleotide triphosphates. The reaction solution is thermocycled, that is, subjected to repeated cycles of temperatures that support, respectively, denaturation of double-stranded polynucleotides, annealing of primers to the template, and extension of the primer into a polynucleotide product, also referred to as an amplicon. The amount of amplicon amplification product may be determined after each thermocycle, or at least several thermocycles, and thus the progress of the reaction can be followed. Devices, methods, and systems of the invention provide in one microfluidic device a chamber for conducting an amplification reaction, and connected thereto a separation channel for measuring the amount of amplicon (polynucleotide product) generated in the reaction.

Related applications include using other types of nucleic acid amplification reactions that detect either DNA or RNA targets, including isothermal amplification methods, for the generation of reaction products that indicate the presence (and amount) of the targeted analyte. Although isothermal reactions do not proceed according to discreet cycles defined by temperature excursions, the same principle applies to periodic measurement of the reaction product.

A. Devices

FIG. 1A illustrates an embodiment of a microfluidic device 100 of the invention. The device comprises a chamber 11 for performing reactions.

The chamber 11 is designed to have a volume of about 0.5 µL to about 200 µL. The volume of the chamber 11 can be sized according to the type of reaction conducted therein, and so that the reaction produces an amount of product sufficient to be analyzed, detected, or otherwise used. For example, if the reaction is an amplification reaction, such as polymerase chain reaction (PCR), the desired sensitivity of a PCR assay conducted in the device is a factor in setting the volume of the reaction chamber. If 10 target copies can be reliably amplified, and if the desired sensitivity is 1 copy per microliter, then the reaction chamber volume should be at least about 10 µL. A reaction chamber having a volume of about 0.5 µL, 1.0, 10, 25, 50, 75, 100, 150, or 200 µL is contemplated.

The reaction solution may be introduced into chamber 11 using, for example, access channels 18 and 19. Access channels 18 and 19 lead from access wells 5 and 6 (respectively) to chamber 11. As exemplified here, the access channels may provide access to opposite sides of chamber 11 in order to facilitate the filling of the chamber with a reaction solution while avoiding bubbles or voids within the liquid in the chamber. For example, a solution introduced in access well 5 can be transported through access channel 18, enter and fill chamber 11, and exit the chamber through access channel 19.

Fluid movement into the chamber 11 can be caused, for example, by capillary action, by applying a pressure to the fluid, or by electrokinetics. The pressure may be a positive pressure applied at the first access well, or a negative pressure applied at the second access well. Typically, the capacity of the first access well should be large enough to accommodate a volume of fluid sufficient to fill the chamber and at least a portion of the at least two access channels. The capacity of the first access well may be large enough to accommodate a volume of fluid sufficient to fill the chamber, the at least two access channels, and at least a portion of the access wells.

The chamber 11 also is in fluidic communication with an analysis channel network. The analysis channel network comprises a load channel 12, a preload channel 13, a separation channel 14, and, if present, a side channel 21. Load channel 12 leads from chamber 11 to load waste well 3. Separation channel 14 leads from separation head well 4 to separation waste well 1, and intersects load channel 12 at the load channel/separation channel intersection 16. Preload channel 13 leads from the load channel 12 at a position between chamber 11 and load channel/separation channel intersection 16 to a preload waste well 9. The point at which preload channel 13 meets load channel 12 may also be referred to as the load channel/preload channel junction 15. Side channel 21 leads from the load channel 12 at a position between chamber 11 and load channel/preload channel junction 15 to a side waste well 8. The point at which side channel 21 meets load channel 12 may also be referred to as the load channel/side channel junction 17. The position of the junction between the load channel and the side channel, junction 17, may differ from that shown in FIG. 1A. For example, when the side channel is used to deliver polynucleotide length markers to the load channel for mixing with the sample components, the side channel may join with load channel 12 between junction 15 and intersection 16. There are otherwise no particular conditions regarding the location of junction 17. In some embodiments, a focus dye channel 22 leads from separation channel 14 to a focus dye well 2. The focus dye channel/separation channel junction is typically located downstream of the portion of the separation channel that is used as a detection region.

In some embodiments, well 7, is in fluidic communication with chamber 11 via channel 20. Such a well provides fluidic and electrochemical communication from the well to the reaction chamber 11.

An electrode (not shown) is present in each of wells 1, 2, 3, 4, 7, 8, and 9. An electrode may optionally be present in wells 5 and/or 6. The electrodes are independently controllable. By applying a potential difference between two electrodes or applying potential differences such that a particular current is achieved through a particular electrode (or combinations of potential and galvanic control of the set of electrodes), electrokinetic transport can be induced along the pathway between two points in the microfluidic device. An electrode present in well 7 can be used to apply a potential difference between the chamber 11 and another point within the analysis channel network, generally another well, such as load waste well 3 or preload waste well 9. Thus, the potential difference between well 7 and another one of the wells can be used to induce electrokinetic transport of reaction solution components from the chamber and into the analysis channel network towards either load waste well 3 or preload waste well 9, for example, as described below. Electrodes can be provided as external electrodes that are lowered into the wells, or electrodes can be microfabricated as part of the device itself.

As shown in FIG. 1A, well 10 is not used in the particular configuration of device 100.

The distances along load channel 12 from chamber 11 to intersection 16 ("distance A") and from junction 15 to intersection 16 ("distance B"), shown in FIG. 1B, are designed to meet conditions based on the mobility, and thus the velocity, of the components to be analyzed using device 100. Exemplary lengths for distance A and distance B are 0.1-2 cm and 0.01-0.2 cm, respectively. These ranges generally reflect the length of the channel segments that are practically applied for the analysis of ~100-500 base pair nucleic acid fragments. Detailed design criteria and the relationship between these segment lengths are described below. With these design criteria, device 100 is able to perform the methods of the invention and thereby provide results more quickly than otherwise possible because some steps can be performed simultaneously.

Charged components (molecules having a net positive or net negative charge) in the reaction solution in chamber 11 can be analyzed as follows. Consider the electrophoretic mobility $\mu_i$ of each charged component in the reaction solution that is to be analyzed. For a given electric field E established by applying a potential difference across a pair of electrodes, the velocity $v_i$ of a reaction solution component is $v_i = \mu_i E$. Of the components to be analyzed, determine the fastest and slowest moving components. It should be recognized that charged species may be present in the reaction solution that are not components of interest for the analysis. Such other charged species are not to be included in this determination. For example, when the devices and methods disclosed herein are applied to real-time PCR analyses, the charged species of interest include the amplicons generated from the primer pairs contacted with the reaction solution. Designate the electrokinetic velocities as $v_{fast}$ and $v_{slow}$, respectively. The length along load channel 12 for distance A and distance B should be such that the following conditions are met:

$$v_{fast}(t_{load}) < \text{distance } A \quad (1)$$

$$v_{slow}(t_{load} + t_{preload} + t_{load}) > \text{distance } A \quad (2)$$

$$v_{slow}(t_{load}) > \text{distance } B \quad (3)$$

where $v_{fast}$, $v_{slow}$, distance A, and distance B are as defined above, and $t_{load}$ and $t_{preload}$ are time periods during which a potential difference is applied to perform a load step and a preload step, respectively. Thus, during the time period $t_{load}$, a component that has a mobility $\mu$ will move a distance $\mu E(t_{load}) = v(t_{load}) = D_{load}$. The application of the relative distance traveled during a load step and a preload step to the device design is addressed now, while the steps themselves are explained further below.

Where there is only one sample component of interest, the fast and slow species will be the same species, and accordingly $v_{fast} = v_{slow}$ in the above conditions. More typically, at least two species that are of interest will be present in the reaction solution. For example, the two species may comprise an analyte and a positive control, or two different analytes. Where the reaction is an amplification reaction, the analytes are amplification products. Where the reaction is a PCR reaction, the analytes are amplicons produced by primer pairs that amplify a target sequence.

A wide range of design solutions fulfill the conditions of equations (1)-(3). There is not a unique solution. Rather, one could fix the time periods and determine the range of valid distances A and B, or one could fix the distances A and B and determine operating range of times for the load and preload steps.

The conditions set forth the following requirements. Equation (1) provides that the fastest moving species does not travel the distance A (from chamber 11 to intersection 16) during the time of duration of a "load step." Equation (2) provides that the slowest moving species will at least travel the distance A during the time of duration of two "load steps" and one "preload step." Finally, equation (3) provides that the slowest species will at least travel the distance B (from junction 15 to intersection 16) during the time of duration of a "load step." The import of these steps and the various criteria for movement can be understood in view of the method steps described below.

One embodiment contemplates the analysis of polynucleotide products. For example, the reaction may be a nucleic acid amplification reaction that generates nucleic acid amplicons. Typical nucleic acid amplicon products have a mobility of about $2\text{-}3 \times 10^{-4}$ cm$^2$/sV. Application of an electric field of 100 V/cm will cause the amplicon products to migrate at a velocity of 0.02-0.03 cm/s. Setting $t_{load}$ and $t_{preload}$ to 10 s and 20 s, respectively, results in the following design criteria for the load channel.

$$v_{fast}(t_{load}) < \text{distance } A; 0.03(10) = 0.3 \text{ cm} < \text{distance } A \quad (1')$$

$$v_{slow}(t_{load} + t_{preload} + t_{load}) > \text{distance } A; 0.02(40) = 0.8 > \text{distance } A \quad (2')$$

$$v_{slow}(t_{load}) > \text{distance } B; 0.02(10) = 0.2 \text{ cm} > \text{distance } B \quad (3')$$

Thus, for the given step times, it can be determined that distance B should be less than 0.2 cm, while the distance A should be greater than 0.3 cm and less than 0.8 cm. The distance along load channel 12 from chamber 11 to junction 17 is obtained by subtracting distance B from distance A. Referring to the distance from chamber 11 to junction 17 as distance C (see FIG. 1B), the above conditions can be expressed in terms of the segments lengths distance B and distance C. Thus, for the above example, $$\text{distance } C > 0.3 \text{ cm} - \text{distance } B \quad (1')$$

$$\text{distance } C < 0.8 \text{ cm} - \text{distance } B \quad (2')$$

$$\text{distance } B < 0.2 \text{ cm} \quad (3')$$

Accordingly, the above equations provide the range of valid solutions for a given set of $t_{load}$ and $t_{preload}$ times and analyte velocity. Similarly, one can fix the load channel segment lengths and analyte velocity and determine the appropriate $t_{load}$ and $t_{preload}$ times.

These equations can also be solved graphically. FIG. 1C shows a graph illustrating the range of valid solutions for the length of load channel segments. The hatched area of the graph indicates the range of segment lengths for the load channel from junction 15 to intersection 16 (Distance B) and from the chamber to junction 15 (Distance C) that comply with the design criteria set forth herein. The three lines plotted on the graph illustrate the limits imposed by the three equations.

Fabrication of microfluidic devices according to the invention generally involves preparing devices with fluidic features (e.g., channels, chambers) with different dimensions, particularly with different depths. For example, access channels 18 and 19 and chamber 11 are typically deeper, e.g., 50-500 μm deep, in order to accommodate the necessary sample volume for analysis. On the other hand, the analysis channel network typically comprises channels with a small cross-section that are less deep, e.g., 20-60 μm deep. By making the cross-section and the overall volume of the analysis channel network small, only a small fraction of the reaction solution needs to be removed for analysis and the large hydrodynamic flow resistance to entry into the channel network serves as a valve, as noted above.

A microfluidic device could be made from any suitable material known to one skilled in the art. As disclosed in U.S. Pat. No. 8,394,324, methods for preparing such devices are known in the art. Polymethylmethacrylates and cyclic olefin polymers are suited to preparing channels of differing dimensions (i.e., depths). The materials are selected for their compatibility with microfabrication techniques, which includes joining the materials to produce a device. For example, devices can be formed from polymer materials such as polymethylmethacrylate (PMMA), cyclic olefin polymers (COP) or cyclic olefin copolymers (COO), polycarbonate (PC), polyesters (PE), and other suitable polymers or elastomers, glass, quartz, and semiconductor materials, and the like.

Cyclic olefin copolymers (COC) are produced, for example, by chain copolymerization of cyclic monomers such as bicyclo[2.2.1]hept-2-ene (norbornene) or 1,2,3,4,4a,5,8,8a-octahydro-1.4:5,8-dimethanonaphthalene (tetracyclododecene) with ethene. Examples of COC's include Ticona's TOPAS® and Mitsui Chemical's APEL™. COC's may also be prepared by ring-opening metathesis polymerization of various cyclic monomers followed by hydrogenation. Examples of such polymers include Japan Synthetic Rubber's ARTON and Zeon Chemical's Zeonex® and Zeonor®. Polymerizing a single type of cyclic monomer yields a cyclic olefin polymer (COP). PC, such as Mitsubishi's Lupilon® polycarbonate, and PMMA, such as Evonik CYRO's Acrylite® line of acrylates (e.g., S10, L40, M30) are suitable plastics for fabricating microfluidic devices.

Generally, such polymers are available in many grades. Depending on the application, an FDA-approved grade may be appropriate, though other types of grades may suffice. Other considerations regarding the choice of substrate for a microfluidic device include ease and reproducibility of fabrication, and low background in an optical measurement. These parameters can be readily optimized by those of skill in the art.

Typically, microfluidic devices that comprise a network of chambers, channels, and wells may be prepared from two or more substrate layers that are joined together to form a device. The manufacturing techniques for such devices, commonly referred to as microfabrication techniques, are well-known in the art. In one example of a device preparation method, microfluidic chamber and channel features are microfabricated in the first surface of a substrate that comprises a first layer, and a second layer is joined to the first surface of the first layer in which the features were microfabricated to thereby enclose the features. Multilayered devices can also be prepared and are well-known in the art.

In one embodiment, a device may be prepared by joining a polymeric thin film to a substrate first surface having a microfluidic network defined therein (i.e. a surface that presents trenches, indentations, grooves, holes, etc.) to thereby enclose the network. The thin film may have a thickness of about 20 μm to about 500 μm, or about 50 μm to about 200 μm. The thin film may be selected according to the uniformity of thickness, availability, ease of joining, clarity, optical properties, thermal properties, chemical properties, and other physical properties. Joining techniques include lamination, ultrasonic welding, IR welding, and the like, as are known in the art. The thin film material could be the same or different as the substrate to which it is joined.

B. Methods of Using the Devices

Devices that satisfy the design conditions described herein can be operated using the methods disclosed herein to analyze a time series of two or more samples from the chamber. The methods are useful for analyzing the chamber contents as a function of time. The methods find use in following the progress of reactions performed in the chamber or monitoring the contents of the chamber over time. For example, the growth in the amount of amplicon produced in a nucleic acid amplification reaction or the kinetics of enzymatic reactions or binding reactions can be determined. One particular application involves following the progress of a PCR reaction. PCR amplicons can be analyzed by removing a sample from the chamber after each cycle, or after selected cycles, and subjecting each sample to a separation analysis in the analysis channel network.

FIG. 2 illustrates the general flow of sample components in the device for one method. In FIG. 2, the main device features are shown using the same numbering as in FIG. 1. The features include a chamber 11, a load channel 12 that leads from chamber 11 to load waste well 3, a preload channel 13 that leads from junction 15 with load channel 12 to preload waste well 9, and separation channel 14, which leads from separation head well 4 to separation waste well 1 and intersects load channel 12 at intersection 16.

The general order and flow direction of sample components is indicated by dashed lines (I)', (I)'', (II), and (III). First, sample components are moved from chamber 11 towards load waste well 3, resulting in the movement indicated by (I)' and (I)''. According to this method, two different samples are present in load channel 12, which are represented by (I)' and (I)''. The first time that sample components are removed from chamber 11, however, no previous sample is present in load channel 12 thus there is not yet a flow of components represented by (I)''. The first time sample components are removed from chamber 11, there is a movement of sample components as indicated by (I)', from the chamber and into load channel 12.

Next, sample components are moved from chamber 11 towards preload waste well 9, according to the movement indicated by (II). Thus, for movement (II), sample components moved into load channel 12 as shown by (I)' continue to move along load channel 12 and then leave load channel 12 to enter preload channel 13. In addition, sample components from chamber 11 will continue to move into load channel 12. Thus due to the combination of movements indicated by (I)' and (II), sample components will fill load channel 12 up to junction 15, and might also be found in preload channel 13.

After some time has passed and it is appropriate to remove a next set of sample components for analysis, sample components are moved from chamber 11 towards load waste well 3, resulting in the movement indicated by (I)' and (I)". A next set of sample components will enter load channel 12 as indicated by (I)' as described above for the initial set of sample components previously moved into load channel 12. And, this time, because sample components had previously been moved into load channel up to junction 15, these sample components will be moved along load channel 12, across the load channel/separation channel intersection 16 and towards load waste well 3. Likewise if additional sets of sample components are removed from chamber 11 at later times for analysis, there will be two different sample component sets present in load channel 12—the previous set of sample components removed from chamber 11 will be present in load channel 12 up to about junction 15, while the current set of sample components removed from chamber 11 will have just entered load channel 12.

The third type of movement of sample components is indicated by (III). Sample components previously moved into the load channel/separation channel intersection 16 are injected into separation channel 14 and moved towards separation waste well 1. As the sample components move along separation channel 14, the components are separated and detected. The timing, coordination, and duration of these various movements will be further explained in conjunction with FIGS. 3 and 4.

FIGS. 3A-C illustrates the patterns for applying a voltage across various locations in the microfluidic device so as to induce the movements (I)', (I)", (II), and (III) discussed in connection with FIG. 2. The repeated application of a voltage difference according to the three patterns VD1, VD2, and VD3 shown in FIGS. 3A-C in the microfluidic devices described herein results in the rapid analysis of a series of sample components from chamber 11. FIG. 3A shows the application of a first voltage VD1 across chamber 11 and load waste well 3. The electrode 1e associated with chamber 11 is illustrated in the figure to be located in chamber 11, but this is to simplify the visual representation for the embodiment of the device described herein. For the device described in FIG. 1A, an electrode at well 7, which is in electrochemical communication with chamber 11 via channel 20, is typically used to apply the first and second voltage as described in connection with FIGS. 3A and 3B. To move, for example, anionic analyte components from chamber 11 into load channel 12, the electrode 3e in load waste well 3 is biased positive (anode) and an electrode 11e in electrochemical contact with chamber 11 is biased negative (cathode). The reverse polarization will cause cationic analyte components to move from chamber 11 into and along load channel 12. During the period that the first voltage is applied, charged analyte components already present in load channel 12 will move along the channel towards load waste well 3, and charged analyte components in chamber 11 will move into load channel 12. Furthermore, the first voltage VD1 of FIG. 3A is applied for a duration such that: (i) the slowest moving analyte component present in load channel 12 can move from junction 15 to at least intersection 16, and (ii) the fastest moving analyte in chamber 11 enters load channel 12 but does not reach intersection 16.

Subsequent to applying a first voltage VD1 as shown in FIG. 3A, the application of a second voltage VD2, as shown in FIG. 3B, between electrode 1e in chamber 11 and electrode 9e in the preload waste well 9 will cause charged analyte components to move along load channel 12 and into preload channel 13. In addition, charged analyte components from chamber 11 will continue to enter load channel 12. The second voltage is applied for a period of time such that sample components will have been moved from chamber 11 into load channel 12 up to the junction with the preload channel (junction 15), a position close to separation channel 14, and into preload channel 13. Furthermore, the second voltage VD2 is applied for a duration such that in the period of time that the first voltage is applied two times and the second voltage applied once, the slowest charged analyte component moves at least the distance from chamber 11 to load channel/separation channel intersection 16.

Also subsequent to applying a first voltage VD1 as shown in FIG. 3A, the application of a third voltage VD3 between electrode 4e in separation head well 4 and electrode 1e in separation waste well 1, as shown in FIG. 3C, will cause charged analyte components present in and around load channel/separation channel intersection 16 to move into separation channel 14. Charged analyte components present in the load channel/separation channel intersection region can be injected into separation channel 14. Injected material is not limited strictly to analyte components within the literal intersection of the two channels. Instead, as is known in the art, analyte components present in the literal intersection and in portions of load channel 12 adjacent to the intersection may also be injected into separation channel 14 in this process. The extent to which analyte components will be injected from the intersection region depends on the timing and magnitude of pullback voltages applied to the relevant wells. The third voltage VD3 is applied for a time period sufficient to perform the separation and analysis of the analyte components in separation channel 14. The time required depends on the electric field strength, the mobility of the analyte in the separation medium, the distance from intersection 16 to the point of detection, and the like. These factors can be optimized for rapid separation times while maintaining suitable detection sensitivity and resolution.

FIG. 4A illustrates an exemplary protocol for the order and timing of the steps in one method of performing a reaction and periodically measuring the reaction products according to the invention. The protocol comprises four types of steps: (i) a reaction period in a chamber, (ii) moving sample components from the chamber towards a load waste well, (iii) moving sample components from the chamber towards a preload waste well, and (iv) separation analysis. In FIG. 4A, five reaction periods and the subsequent five separation analyses of the reaction products produced after each of the reaction periods are performed. As can be appreciated from the figure, aside from the start-up of the first reaction period and the wind down of the final separation analysis, there are two steps being conducted simultaneously. Were there to be no overlap of any of the steps, the entire process would take 510 seconds. By performing the reaction and separation analysis in a device according to a method disclosed herein, the entire process of five cycles would take 390 seconds according to the time parameters set in this example.

A suitable reaction period is governed by, for example, a time period of interest for incubating the reaction solution, or the time necessary to complete a thermal program. Thus, a reaction performed at a constant temperature may be sampled periodically. The time periods may be constant or varying. Or, a thermal cycle, in which the temperature of the reaction solution is raised and lowered, may constitute a reaction period. The thermal cycle may be a PCR cycle. More than one thermal cycle may be performed during a reaction period, as is described in greater detail below with FIGS. 4B and 4C. The moving steps (ii) and (iii) and separation step (iv) correspond to the application of a first voltage, a second voltage, and a third voltage, as described in FIGS. 3A-C. As illustrated in FIG. 4A, the reaction period is 30 seconds, the first voltage is applied for a 10 second length of time, the second voltage is applied for a 20 second length of time, and the third voltage is applied for a 50 second length of time.

The protocol illustrated in FIG. 4A first includes a reaction period, followed by application of a first voltage VD1 for a first length of time to move sample components from chamber 11 towards load waste well 3 and then application of a second voltage VD2 for a second length of time to move sample components from chamber 11 towards preload waste well 9. At this point, the reaction products generated up to the first reaction period have been moved up load channel 12 to junction 15. Because no sample components have yet advanced to intersection 16 a separation analysis is not necessary, however one may apply a third voltage VD3 for a third length of time without adverse effect.

Next, a second reaction period is performed, followed again by application of a first voltage VD1 for a first length of time. This time, sample components of the first reaction period are moved towards load waste well 3 and into intersection 16, while sample components of the second reaction period are moved into load channel 12. At this point, a second voltage VD2 is applied across chamber 11 and preload waste well 9, and a third voltage VD3 is applied across separation head well 4 and separation waste well 1. As illustrated, these two processes are carried out in parallel. The second and third voltages are applied beginning at about the same time. The step of applying a second voltage ends before the step of applying a third voltage (separation step). While the step of applying a third voltage continues, the next reaction period can be initiated. Thus, the reaction period is performed entirely within the separation analysis period.

By adjusting the separation analysis parameters (e.g., speed of analyte migration, distance to detector, etc.) and reaction period parameters (e.g., thermocycler temperatures, times, ramp rates, etc.) these periods can be adjusted to end at about the same time. By having these steps end at about the same time, the subsequent step of moving the newly generated reaction products from chamber 11 towards load waste well 3 can start immediately.

Although FIG. 4A shows an exemplary protocol consisting of five reaction periods and five separation analyses, the number of reaction periods and separation analyses can be freely adjusted according to the needs of the experiment. For example, a series of at least two, five, ten, fifteen, twenty, or twenty-five, or as many as 50 separation analyses may be conducted on the contents of the reaction solution in the chamber. Any number of reaction periods can be conducted before the first separation analysis. By delaying the start of the separation analysis, the amount of product may build up to a level that is more readily measured. In some embodiments, the analysis may be stopped when a product peak is detected beyond a threshold level, or after a predetermined number of reaction periods following the detection of a product peak.

The separation analysis can also be performed after every other, or every third reaction period, or after any particular set of reaction periods, instead of after each reaction period. The reaction periods need not all be of the same duration, but can be varied as necessary or desired. Where the reaction is a nucleic acid amplification reaction, such as PCR, one may perform from about 8 to about 17 thermocycles before analyzing the amount of product generated. Thereafter, the amount of product may be analyzed after every, or every other, thermocycle, for example. The total number of thermocycles performed may be about 35 to about 45 cycles, depending on the detection sensitivity, amplification efficiency, and amount of target expected for the samples, as well as the chamber volume and analysis channel network volume. Fewer cycles may be sufficient if the amount of target analyte expected in the assay sample is large.

Table 1 illustrates how one can optimize the overall analysis time by adjusting the number of thermocycles and CE separation analyses conducted. For example, the CE analysis can start with e.g., the tenth reaction cycle, that is, after 9 reaction cycles have been performed. Furthermore, the CE analysis can be conducted after every other reaction cycle instead of after every reaction cycle. Another variation is to conduct the CE analysis after every other reaction cycle until a product peak is detected, and then conduct the analysis after every cycle to define the growth curve with greater precision. This CE analysis can optionally be stopped after a preset number of analyses, based on the presumption that the growth curve will be adequately defined after a certain number of cycles. For example, in certain embodiments a growth is sufficiently defined after 8, after 10, after 12, or about after 14 cycles following the detection of a product peak. The "every cycle on peak detection" mode illustrated in Table 1 shows an example wherein a product peak is detected in cycle 12, and thereafter a CE analysis is conducted every cycle beginning with cycle 14 for, e.g., 10 consecutive cycles and then CE analysis is stopped. The gap between cycle 12 and cycle 14 occurs because the result of the analysis of cycle 12 would not be known until after reaction cycles 13 and 14 are already completed. If a product peak is not detected, then the CE analysis would continue every other cycle for the duration of the analysis, whereupon the sample would be reported to be a "negative sample."

TABLE 1

| | CE Analysis Mode | | |
|---|---|---|---|
| Cycle Number | Every Cycle | Every 2 Cycles | Every Cycle on Peak Detection |
| 1-9 | — | — | — |
| 10 | CE | CE | CE |
| 11 | CE | — | — |
| 12 | CE | CE | CE |
| 13 | CE | — | — |
| 14 | CE | CE | CE |
| 15 | CE | — | CE |
| 16 | CE | CE | CE |
| 17 | CE | — | CE |
| 18 | CE | CE | CE |
| 19 | CE | — | CE |
| 20 | CE | CE | CE |
| 21 | CE | — | CE |
| 22 | CE | CE | CE |
| 23 | CE | — | CE |
| 24 | CE | CE | — |
| 25 | CE | — | — |
| 26 | CE | CE | — |
| 27 | CE | — | — |
| 28 | CE | CE | — |
| 29 | CE | — | — |
| 30 | CE | CE | — |
| 31 | CE | — | — |
| 32 | CE | CE | — |
| 33 | CE | — | — |
| 34 | CE | CE | — |
| 35 | CE | — | — |
| 36 | CE | CE | — |
| 37 | CE | — | — |
| 38 | CE | CE | — |

TABLE 1-continued

| | CE Analysis Mode | | |
|---|---|---|---|
| Cycle Number | Every Cycle | Every 2 Cycles | Every Cycle on Peak Detection |
| 39 | CE | — | — |
| 40 | CE | CE | — |
| Number of CE Analyses | 31 | 16 | 12 |
| Assay Time (min) | 35.5 | 28 | 17.5 |

As seen in Table 1, further time savings can be achieved by adjusting the number of CE analyses conducted. Rather than assaying the reaction every cycle, wherein 31 CE runs would be necessary (in this example), in some embodiments the CE analysis may be preset to occur after every other reaction cycle, wherein only 16 CE runs are necessary (in this example). The benefit of a time savings of about 7.5 minutes (as estimated for the time parameters presented in FIGS. 4A and 4B) should be balanced against the loss of precision in defining the growth curve. One of skill in the art can readily determine which factor is more important in the application of the method. Other variations in the number of CE analyses are of course possible. In other embodiments, the frequency of CE analysis is changed from every other cycle to every cycle once a product peak is detected, wherein 12 CE analyses would be conducted (in this example). Here, a time savings of about 18 minutes, or about half of the every-cycle-mode assay time can be achieved with very little change in the precision of the growth curve.

FIG. 4B illustrates an exemplary protocol for the order and timing of the steps in an embodiment in which two reaction cycles are conducted and the product resulting from the second of the two cycles is measured. In other words, in FIG. 4B, every other reaction cycle is analyzed. The protocol again comprises the same four types of steps: (i) a reaction period in a chamber, (ii) moving sample components from the chamber towards a load waste well, (iii) moving sample components from the chamber towards a preload waste well, and (iv) separation analysis. In FIG. 4B, eight reaction periods and the subsequent four separation analyses of the reaction products produced after every other reaction period are shown. As can be appreciated from FIG. 4B when compared with FIG. 4A an extra reaction period is inserted directly following the one carried out while the separation analysis is conducted, and the subsequent steps await the end of the second of the reaction period. Whereas the time to completely process five cycles and five analyses required 390 seconds for the embodiment of FIG. 4A, in the embodiment of FIG. 4B, six reaction cycles and the analysis of every other (three) would require the same 390 seconds. Further time savings would be achieved with more cycles.

Similarly. FIG. 4C illustrates an exemplary protocol for the order and timing of the steps in an embodiment in which two reaction cycles are conducted and the product resulting from the first of the two cycles is measured. In FIG. 4C as well, every other reaction cycle is analyzed. The protocol again comprises the same four types of steps: (i) a reaction period in a chamber, (ii) moving sample components from the chamber towards a load waste well, (iii) moving sample components from the chamber towards a preload waste well, and (iv) separation analysis. In FIG. 4C, eight reaction periods and the subsequent four separation analyses of the reaction products produced after the first reaction period of each pair of periods are shown. As can be appreciated from FIG. 4C when compared with FIG. 4B, after the first reaction period of the pair, a sample is removed and subjected to sample movements (ii) and (iii), and then the second reaction period occurs while the separation analysis of a previous sample is carried out. Whereas the time to completely process five cycles and five analyses required 390 seconds for the embodiment of FIG. 4A, and the embodiment of FIG. 4B performed six reaction cycles and the analysis of every other (three) in the same 390 seconds, in the embodiment of FIG. 4C, six reaction cycles and the analysis of three requires only 360 seconds. Further time savings would be achieved with more cycles.

FIG. 5 illustrates the general flow of sample components in the device for another method according to the invention. In FIG. 5, the main device features are shown using the same numbering as in FIG. 1. The features include a chamber 11, a load channel 12 that leads from chamber 11 to load waste well 3, a preload channel 13 that leads from junction 15 with load channel 12 to preload waste well 9, and separation channel 14, which leads from separation head well 4 to separation waste well 1 and intersects load channel 12 at intersection 16.

The general order and flow direction of sample components is indicated by dashed lines (I), (II), and (III). First, sample components are moved from chamber 11 towards preload waste well 9, resulting in the movement indicated by (I). The first time that sample components are removed from chamber 11, no previous sample is present in load channel 12 thus there is not yet a set of sample components to be analyzed in the separation channel.

Next, the sample components that were moved into preload channel 13 as a result of movement (I) are sent back in the opposite direction towards load channel 12 and then at least a portion of those sample components are moved along load channel 12 towards load waste well 3 and occupy the load channel/separation channel intersection 16, according to the movement indicated by (II). Thus, due to the combination of movements indicated by (I) and (II), sample components generally will fill load channel 12 up to, at, and past intersection 16, and may also be found in preload channel 13.

The third type of movement of sample components is indicated by (III). Sample components previously moved into the load channel/separation channel intersection 16 are injected into separation channel 14 and moved towards separation waste well 1. As the sample components move along separation channel 14, the components are separated and detected. The timing, coordination, and duration of these various movements will be further explained in conjunction with FIGS. 6 and 7.

Movements (I) and (III) can be conducted simultaneously because the movement paths do not intersect or overlap. The step that precedes each of movements (I) and (III), a reaction period in chamber 11 (precedes (I)), and movement (H) (precedes (III)) can also be conducted simultaneously, because each these events would not interfere with the other. To the extent that either of the pairs of simultaneous events do not require approximately the same amount of time to perform, the shorter event can be performed at any time within the time period of the longer event. For example, if movement (II) occurs in a shorter time period than a reaction period, then movement (II) can, for example, (i) start at about the same time as a reaction period but end early, (ii) start during the reaction period such that the two will end at about the same time, or (iii) start and end within the time for one reaction period. However, it should be noted that part of the shorter event could even occur outside the time period required for performing the longer event. Particularly if the other pair of events are not approximately equal in time, the relative timing of the four events might overlap differently, with different combinations of events occurring at the same time so long as the performance of one does not interfere with the performance of the other. For example, the reaction period could also overlap with movement (III). On the other hand, the reaction period and movement (I) would likely interfere, and movements (I) and (II), and (II) and (III) would interfere with each other. Nonetheless, to the extent that a pair of events, such as movements (I) and (III) are roughly equal in time, then the other pair of events, the reaction period and movement (II) would both occur when movements (I) and (III) do not occur.

FIGS. 6A-C illustrates the patterns for applying a voltage across various locations in the microfluidic device so as to induce the movements (I), (II), and (III) discussed in connection with FIG. 5. The repeated application of a voltage difference VD1, VD2, and VD3 according to the three patterns shown in FIGS. 6A-C in the microfluidic devices described herein results in the rapid analysis of a series of sample components from chamber 11. FIG. 6A shows the application of a first voltage VD1 across chamber 11 and preload waste well 9. The electrode 11e associated with chamber 11 is illustrated in the figure to be located in chamber 11, but this is to simplify the visual representation for the embodiment of the device described herein. For the device as described in FIG. 1A, an electrode at well 7, which is in electrochemical communication with chamber 11 via channel 20, is typically used to apply the first voltage as described in connection with FIG. 6A. To move, for example, anionic analyte components from chamber 11 into load channel 12, the electrode 9e in preload waste well 9 is biased positive (anode) and an electrode 11e in electrochemical contact with chamber 11 is biased negative (cathode). The reverse polarization will cause cationic analyte components to move from chamber 11 into and along load channel 12. During the period that the first voltage is applied, charged analyte components in chamber 11 will move into load channel 12 and then preload channel 13. Furthermore, the first voltage of FIG. 6A is applied for a duration such that: (i) the slowest moving analyte component present in chamber 11 can move into preload channel 13.

Subsequent to applying a first voltage VD1 as shown in FIG. 6A, the application of a second voltage VD2 between electrode 9e and electrode 3e, as shown in FIG. 6B, will cause charged analyte components to move out of preload channel 13, back into load channel 12 and towards load waste well 3. The second voltage is applied for a period of time such that sample components will have been moved from preload channel 13 and into intersection 16.

Also subsequent to applying a second voltage as shown in FIG. 6B, the application of a third voltage VD3 between electrode 4e in separation head well 4 and electrode 1e in separation waste well 1, as shown in FIG. 6C, will cause charged analyte components present in and around load channel/separation channel intersection 16 to move into separation channel 14. Charged analyte components present in the load channel/separation channel intersection region can be injected into separation channel 14. Injected material is not limited strictly to analyte components within the literal intersection of the two channels. Instead, as is known in the art, analyte components present in the literal intersection and in portions of load channel 12 adjacent to the intersection may also be injected into separation channel 14 in this process. The extent to which analyte components will be injected from the intersection region depends on the timing and magnitude of pullback voltages applied to the relevant wells. The third voltage is applied for a time period sufficient to perform the separation and analysis of the analyte components in separation channel 14. The time required depends on the electric field strength, the mobility of the analyte in the separation medium, the distance from intersection 16 to the point of detection, and the like. These factors can be optimized for rapid separation times while maintaining suitable detection sensitivity and resolution.

FIG. 7A illustrates an exemplary protocol for the order and timing of the steps in one method of performing a reaction and periodically measuring the reaction products according to the invention. The protocol comprises four types of steps: (i) a reaction period in a chamber, (ii) moving sample components from the chamber towards a preload waste well, (iii) moving sample components from the preload channel towards a load waste well, and (iv) separation analysis. In FIG. 7A, five reaction periods and the subsequent five separation analyses of the reaction products produced after each of the reaction periods are performed. As can be appreciated from the figure, aside from the start up of the first reaction period and the wind down of the final separation analysis, there are two steps being conducted simultaneously. Were there to be no overlap of any of the steps, the entire process would take 610 seconds. By performing the reaction and separation analysis in a device according to a method disclosed herein, the entire process of five cycles would take 470 seconds according to the time parameters set in this example.

A suitable reaction period is governed by, for example, a time period of interest for incubating the reaction solution, or the time necessary to complete a thermal program. Thus, a reaction performed at a constant temperature may be sampled periodically. The time periods may be constant or varying. Or, a thermal cycle, in which the temperature of the reaction solution is raised and lowered, may constitute a reaction period. The thermal cycle may be a PCR cycle. More than one thermal cycle may be performed during a reaction period, as is described in greater detail below with FIG. 7B. The moving steps (ii) and (iii) and separation step (iv) correspond to the application of a first voltage, a second voltage, and a third voltage, as described in FIGS. 6A-C. As illustrated in FIG. 7A, the reaction period is 30 seconds, the first voltage is applied for a 50 second length of time, the second voltage is applied for a 10 second length of time, and the third voltage is applied for a 50 second length of time.

The protocol illustrated in FIG. 7A first includes a reaction period, followed by application of a first voltage VD1 for a first length of time to move sample components from chamber 11 through load channel 12 and into preload channel 13, towards preload waste well 9.

Next, a second reaction period is performed, and during the second reaction period a second voltage VD2 is applied for a second length of time to move sample components from preload channel 13 towards load waste well 3 and into intersection 16. At this point, the chamber contents are ready to be withdrawn for a subsequent analysis, and the previous reaction period's sample components have been moved into the load channel/separation channel intersection region and are ready for separation analysis.

Thus, at this point, a first voltage VD1 is applied across chamber 11 and preload waste well 9, and a third voltage VD3 is applied across separation head well 4 and separation waste well 1. As illustrated, these two processes are carried out in parallel. The first and third voltages may be applied beginning at about the same time.

By adjusting the separation analysis parameters (e.g., speed of analyte migration, distance to detector, etc.) and reaction period parameters (e.g., thermocycler temperatures, times, ramp rates, etc.) these periods can be adjusted to end at about the same time. By having these steps end at about the same time, the subsequent step of moving the newly generated reaction products from chamber 11 towards preload waste well 9 can start immediately.

Although FIG. 7A shows an exemplary protocol consisting of five reaction periods and five separation analyses, the number of reaction periods and separation analyses can be freely adjusted according to the needs of the experiment. For example, a series of at least two, five, ten, fifteen, twenty, or twenty-five, or as many as 50 separation analyses may be conducted on the contents of the reaction solution in the chamber. Any number of reaction periods can be conducted before the first separation analysis. By delaying the start of the separation analysis, the amount of product may build up to a level that is more readily measured. In some embodiments, the analysis is stopped when a product peak is detected beyond a threshold level, or after a predetermined number of reaction periods following the detection of a product peak.

The separation analysis can also be performed after every other, or every third reaction period, or after any particular set of reaction periods, instead of after each reaction period. The reaction periods need not all be of the same duration, but can be varied as necessary or desired. Where the reaction is a nucleic acid amplification reaction, such as PCR, one may perform from about 8 to about 17 thermocycles before analyzing the amount of product generated. Thereafter, the amount of product may be analyzed after every, or every other, thermocycle, for example. The total number of thermocycles performed may be about 35 to about 45 cycles, depending on the detection sensitivity, amplification efficiency, and amount of target expected for the samples, as well as the chamber volume and analysis channel network volume. Fewer cycles may be sufficient if the amount of target analyte expected in the assay sample is large.

The principles of Table 1 can be applied to the embodiment of FIG. 7A as well. Thus the overall analysis time can be shortened by adjusting the number of thermocycles and CE separation analyses conducted in a similar manner. The amount of time savings will of course depend on the reaction and separation parameters applied to the assay.

FIG. 7B illustrates an exemplary protocol for the order and timing of the steps in an embodiment in which two reaction cycles are conducted and the product resulting from the second of the two cycles is measured. In other words, in FIG. 7B, every other reaction cycle is analyzed. The protocol again comprises the same four types of steps: (i) a reaction period in a chamber, (ii) moving sample components from the chamber towards a load waste well, (iii) moving sample components from the preload channel towards a preload waste well, and (iv) separation analysis. In FIG. 7B, six reaction periods and the subsequent three separation analyses of the reaction products produced after every other reaction period are shown. As can be appreciated from FIG. 7B when compared with FIG. 7A, an extra reaction period is inserted directly following the first one that is normally carried out, and the subsequent steps await the end of the second of the reaction period. Whereas the time to completely process five cycles and five analyses required 470 seconds for the embodiment of FIG. 7A, in the embodiment of FIG. 7B, six reaction cycles and the analysis of every other (three) would require only 430 seconds. Further time savings would be achieved with more cycles.

C. Examples

Example 1: PCR Reaction 1-1. Device

A PCR-CE microfluidic device was prepared from an injection molded polycarbonate substrate and polycarbonate film (GE Plastics, 125 µm Lexan 8010), joined by lamination. The microfluidic device design is shown in FIG. 1A. The overall dimensions of the device are about 45.5 mm×25.5 mm×5.5 mm. The reaction chamber has a depth of about 350 and a volume of about 25 µL. The load channel, preload channel, separation channel, and side channel are each about 30 µm deep and 40 µm wide. Electrodes were screen printed on the polycarbonate film prior to lamination. As prepared, the electrodes are positioned to contact solution added to the well in the substrate/film laminated device.

1-2. PCR Reaction Solution

Primers for amplifying an *E. coli* sequence were synthesized with the following sequences and used a primer pair:

SEQ ID NO: 1
(forward primer)    5'-ATCTATGACTGTACGCCACTGTCCCTAG

SEQ ID NO: 2
(reverse primer)    5'-GCCTAGCAAACTCGGAAGATT

PCR reaction solutions were prepared with the following composition: 1×Taq buffer, 3 mM $MgCl_2$, 1.5 U Fermentas Taq polymerase/25 µL, 0.4 µM primer (each), 0.4 mM dNTP, and 100 mg/mL BSA. The amplification target sequence (100 bases) is contained in *E. coli* genome. Genomic *E. coli* DNA was added as the template at a concentration of 10,000 copies/25 µL of reaction solution.

1-3. Device Loading

The microfluidic device of Example 1-1 was prepared for operation as follows. The analysis channel network was filled with a separation gel comprising 200 mM TAPS buffer at pH 8, 2.5% polydimethylacrylamide sieving matrix, and ethidium bromide dimer fluorescent dye. The PCR reaction solution (25 µL) of Example 1-2 was loaded into access well 6 and delivered to chamber 11 by capillary action. Well 7 was filled with PCR buffer. Other wells were filled with separation gel or markers or focusing dye. The distribution of reagents is shown in the table below. Finally, 15 µL of 20 cst silicone oil was added to wells 5 and 6 (inlets to the reaction chamber) and well 7.

| | | Well # | | | | | | |
|---|---|---|---|---|---|---|---|---|
| | 2 | 1 | 3 | 4 | 7 | 8 | 9 | Chamber |
| Solution | Focusing dye | Gel | Gel | Gel | PCR buffer | DNA Markers | Gel | PCR reaction solution |

Gel Buffer: 3 mM $MgCl_2$, 200 mM TAPS, pH 8.0
Gel: 2.5% PDMA31-146, 0.15 µM EthD in gel buffer
Focusing Dye: 0.2 µM 5-carboxytetramethylrhodamine (TAMRA), 0.15 µM EthD in gel buffer
Marker: Fermentas NoLimits DNA: 15, 300, 500 bp (1 ng/µl each) in gel buffer
PCR Buffer: 1×Taq Buffer, 3 mM $MgCl_2$, 0.4 mM dNTP, 100 mg/ml bovine serum albumin (BSA)

The loaded microfluidic device was placed on a thermal cycling device (not shown) consisting of a flat copper plate connected to a thermoelectric heater/cooler module (Model HV56, Nextreme, Durham, N.C.)). A pressure manifold of the kind disclosed in U.S. Pregrant Publ. No. 2010/0200402 (application Ser. No. 12/600,171) to Li et al., which is incorporated herein by reference in its entirety, was lowered onto the wells of the microfluidic device making a pressure-tight seal over all the wells. A pressure of 20 psi was applied through a manifold device equally to all the wells.

1-4. Device Operation

Real-time PCR-CE analysis of the loaded microfluidic device prepared by Example 1-3 was performed as follows. PCR thermocycling protocol was programmed with the following sequence of denaturing, annealing, and extension temperatures and times:

Cycle 1: 98° C. for 60 s, 58° C. for 14 s, and 77° C. for 8 s.
Cycle 2-16: 98° C. for 7 s, 62° C. for 14 s, and 77° C. for 8 s.
Cycle 17-end: 98° C. for 7 s, 62° C. for 14 s, and 77° C. for 39 s.

First, 16 cycles were performed. Then, beginning with cycle 17, sample components of the PCR reaction solution were removed from the chamber by electrophoresis after each PCR cycle, moved to the separation channel and analyzed by electrophoresis. The potential or the current at the electrode in each well was controlled according to the following protocol:

| Step | Time [sec] | Well2 | Well1 | Well3 | Well4 | Well7 | Well 8 | Well9 |
|---|---|---|---|---|---|---|---|---|
| First | 10 | 0.2 uA | -2.2 uA | 1700 V | -2 uA | -15 uA | -5 uA | 0 uA |
| Second | 21 | 0.2 uA | 1500 V | 2 uA | 500 V | -15 uA | -5 uA | 22 uA |
| Third | 29 | 0.2 uA | 1500 V | 2 uA | 500 V | 0 uA | 0 uA | 2 uA |

The first, second, and third steps correspond to the application of a first voltage, second voltage, and third voltage as illustrated in FIGS. 3A-3C. The protocol was initiated 29 seconds after the start of PCR cycle 17. The first step of potential and current control was applied for 10 seconds, the second step conditions were applied for 21 seconds, and the third step conditions were applied for 29 seconds, and then the same protocol of potential and current control for the first, second, and third steps was repeated through to the end of the PCR reaction.

1-5. Results

Figure 8A:
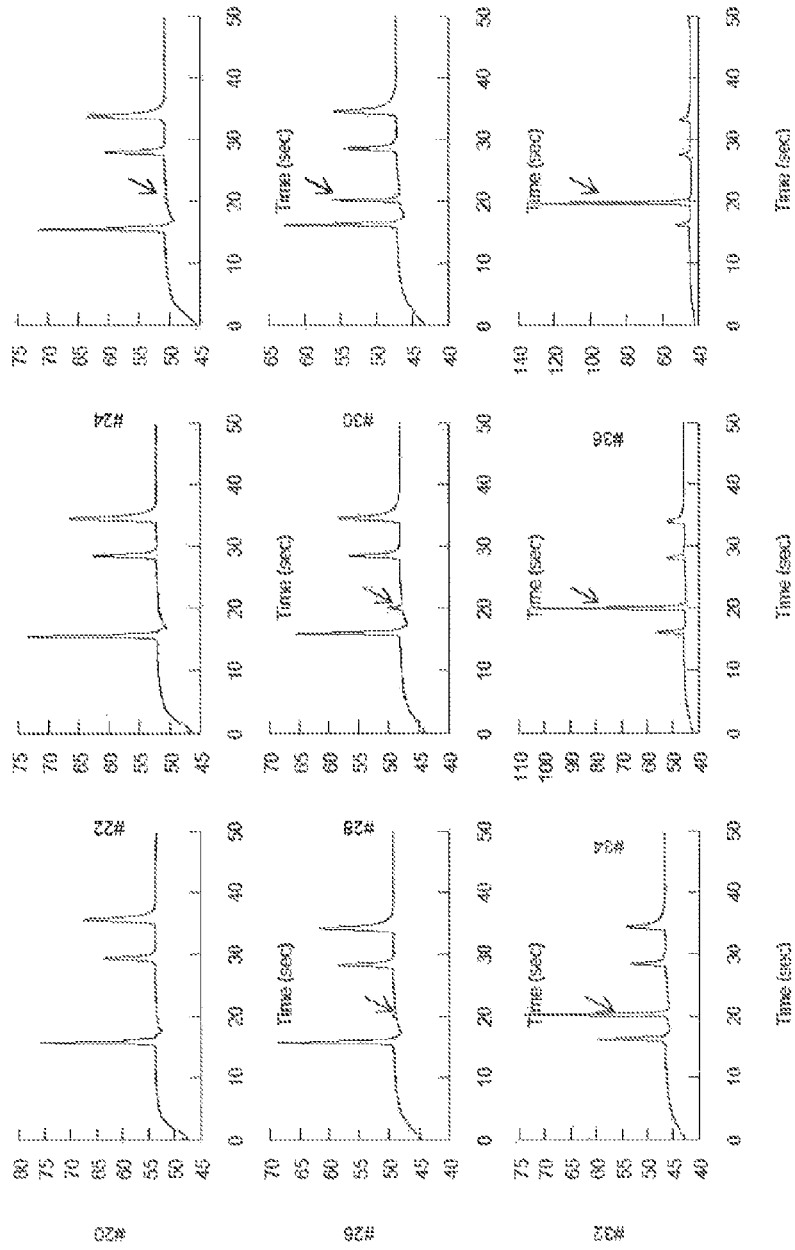
FIGS. 8A and 8B show the results of a real-time PCR-CE analysis conducted according to one embodiment of the invention described in Example 1.

By conducting the PCR and electrophoretic protocol described in Example 1-4, samples of the reaction product were withdrawn after each cycle beginning with cycle 17 and subjected to capillary electrophoresis analysis. The electropherograms analyzing the products of cycle 20, 22, 24, 26, 28, 30, 32, 34, and 36 are shown in FIG. 8A (from left to right, top row to bottom row). In the electropherogram analyzing cycle 20, at the upper left, the three marker peaks are readily apparent. The three peaks are, respectively, 15, 300, and 500 base pair markers. The expected amplicon (100 base pairs) peak is indicated by the arrow. The expected amplicon peak is just perceptible in the upper right electropherogram (analyzing cycle 24), and dominates the electropherogram in the last electropherogram shown (analyzing cycle 36).

Figure 8B:
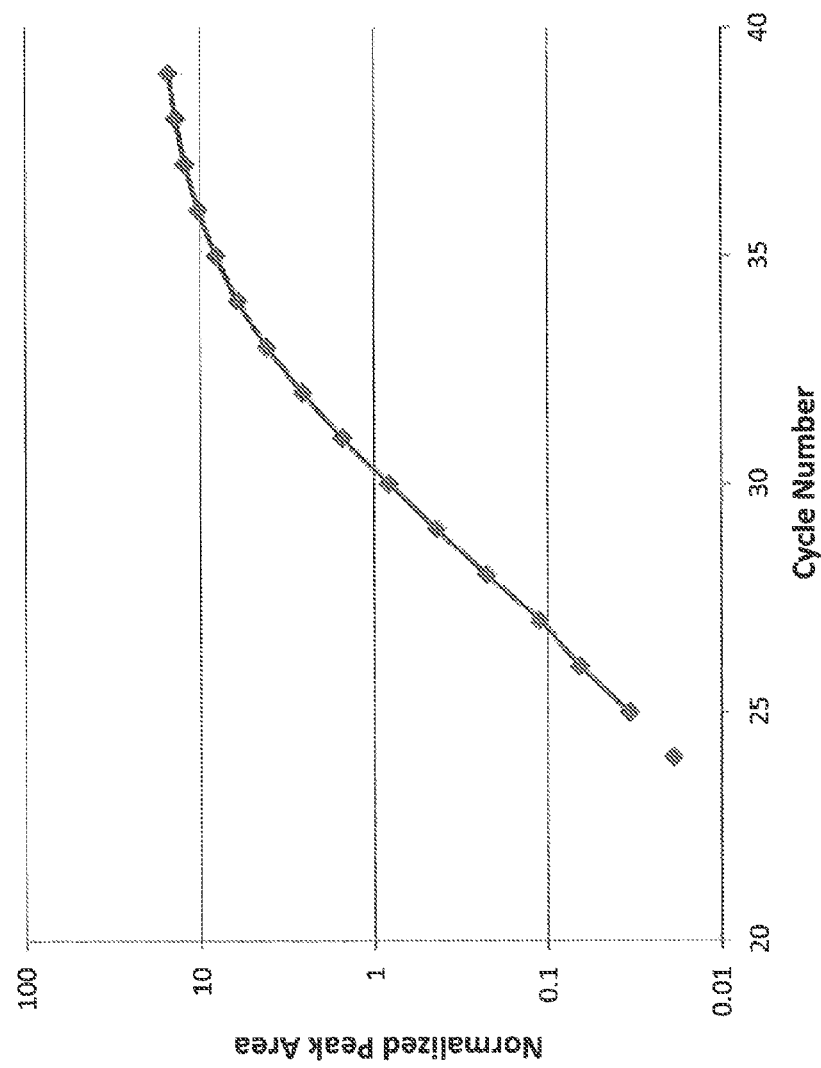

FIG. 8B shows the growth curve of product, that is, the amount of amplicon as a function of cycle number, for the same experiment.

Figure 9A:
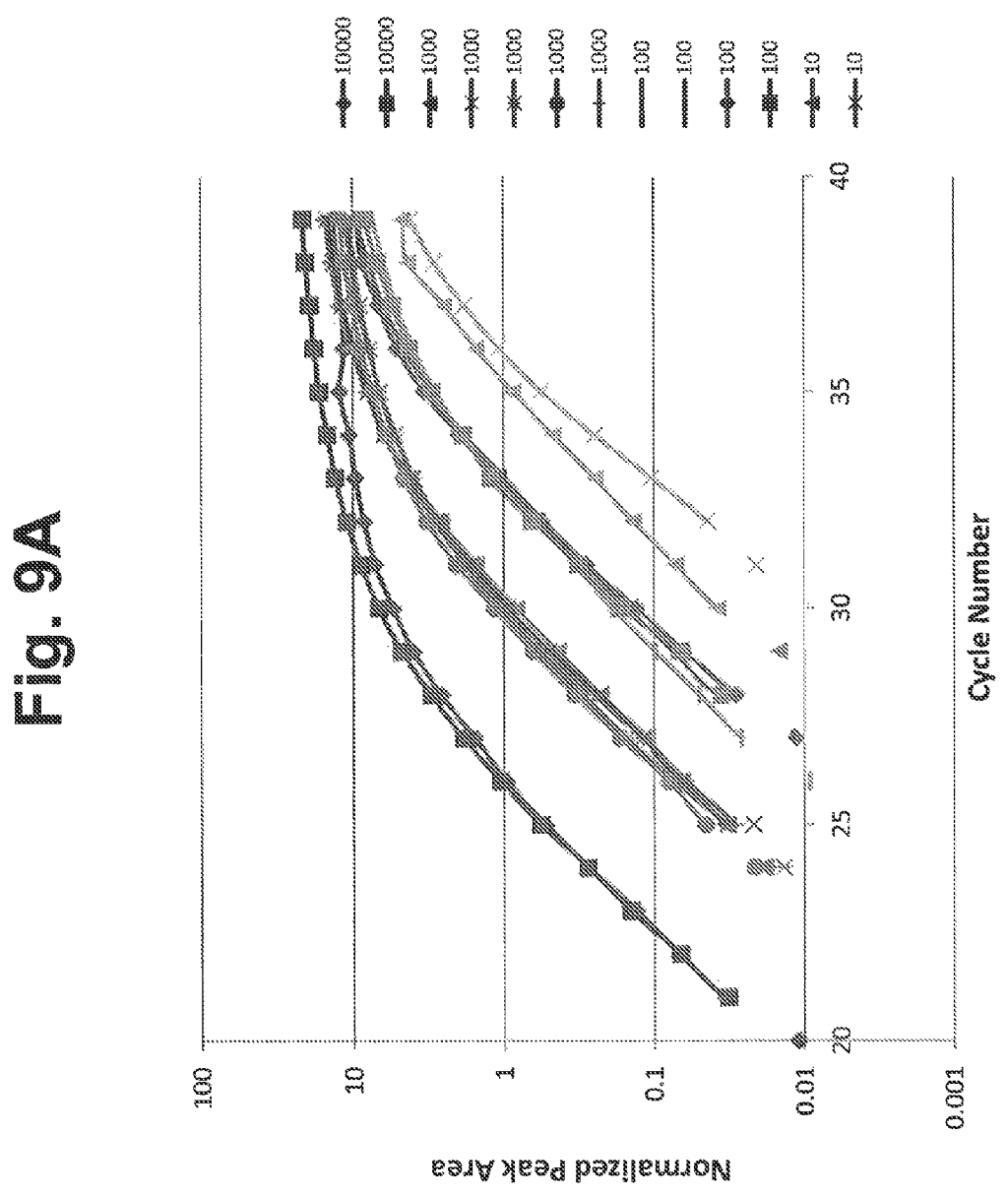
Figure 9B:
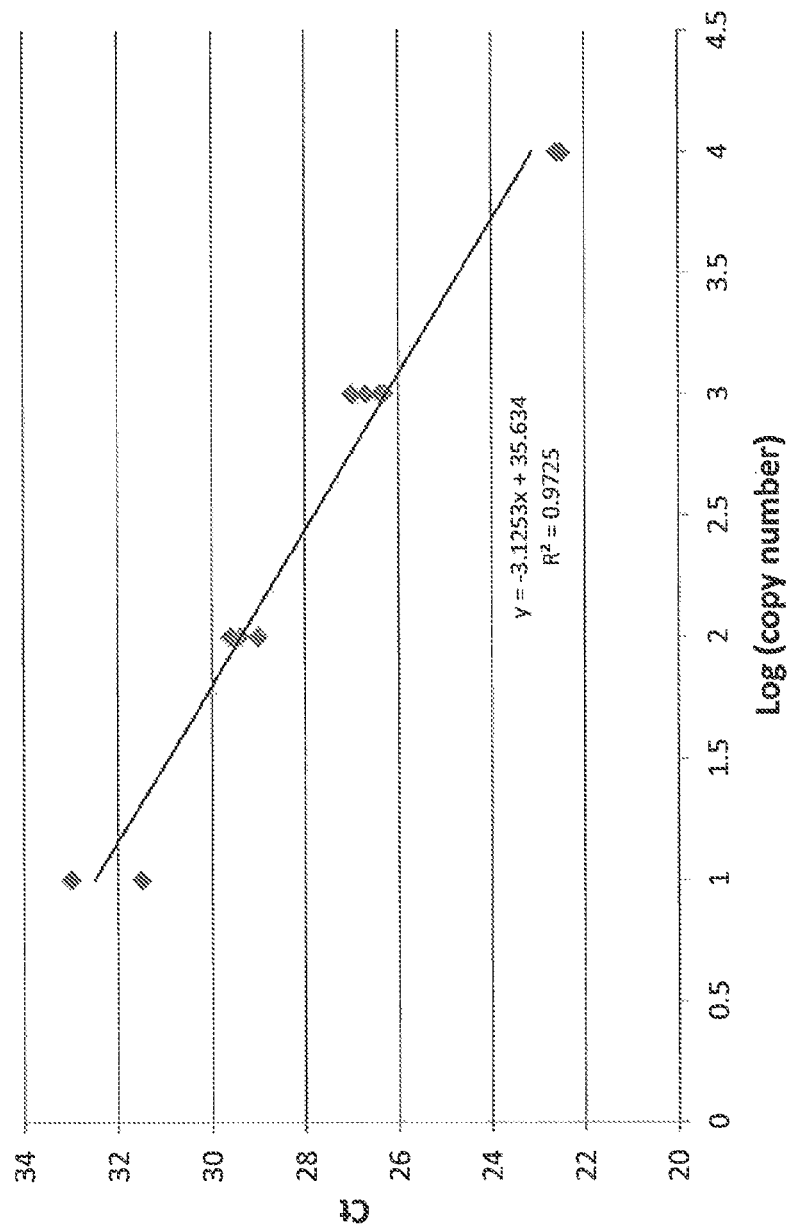

FIG. 9A shows the growth curve for a series of experiments performed as described above, where the amount of target DNA included in the experiment was $10^1$, $10^2$, $10^3$, and $10^4$ per 25 µl of reaction solution. The results indicate that the even the lowest copy number, 10 copies, was detected using the device, method, and system described herein. FIG. 9B shows a plot of the crossing threshold value vs. the log of the number of copies added to the experiments reported in FIG. 9A. The data have a linear correlation.

Example 2: RT-PCR Reaction 2-1. Device

The device described in Example 1-1 was used.

2-2. RT-PCR Reaction Solution

Primers for amplifying hepatitis C virus (HCV) and MS2 bacteriophage, an RNA phage, were prepared and included in an RT-PCR reaction solution. Furthermore, in this example, one primer in each primer was labeled with a fluorescent dye, 5-carboxytetramethylrhodamine (TAMRA).

HCV Primers:

SEQ ID NO: 3
5'-(TAMRA)-GAAAGCGTCTAGCCATGGCGT-3'

SEQ ID NO: 4
5'-CTCGCAAGCACCCTATCAGGCA-3'

MS2 Primers:

SEQ ID NO: 5
5'-GGTATAGTGTGGGAAAAGGTG-3'

SEQ ID NO: 6
5'-(TAMRA)-ACGAGAACGAACTGAGTAAAG-3'

The assay is designed to have two internal controls. The MS2 RNA phage serves as a control for the RNA extraction and purification process. Successful amplification by the MS2 primers of the phage RNA to produce a 380 bp amplicon indicates that the assay procedure would have been sufficient to extract HCV RNA from an HCV viral particle. The use of MS2 bacteriophage as an internal control for RT-PCR assays is described by Dreier et al. in the *Journal of Clinical Microbiology*, 2005, Vol. 43(9), p, 45514557. A plasmid is also included in the reaction solution (below) that incorporates a sequence that can be amplified by the HCV primer pair. Thus, the HCV primer pair will produce two different amplification products if HCV is present in the sample: one product from the internal control plasmid, and one from an HCV viral particle. The respective amplicon lengths are 440 bp for the internal control and 250 bp for HCV. The appearance of the amplification product from the internal control plasmid controls for the proper conditions for the PCR reaction.

RT-PCR reaction solutions were prepared with the following composition:

| | |
|---|---|
| PCR buffer (see below) | 1X |
| dNTP | 0.4 mM |
| KOD exo(-) polymerase (Toyobo Co.) | 0.05 µg/µL |
| HCV primers | 0.4 µM (each) |
| MS2 primers | 0.1 µM (each) |
| DMSO | 5% |
| HCV viral particle | 50 to 50,000 copies/30 µL |
| MS2 viral particle | 40,000 copies/30 µL |
| PCR internal control plasmid | ~1,000 copies/30 µL |

HCV High Positive Control viral particles were obtained from Acrometrix (Benicia, Calif.), a product that is calibrated to the World Health Organization Standard NIBSC 96/798. MS2 bacteriophage, strain 15597-B1, was obtained from Virapur (San Diego, Calif.)

The components were combined, vortexed thoroughly and briefly spun, 30 µL was transferred to a Bioneer RT premix tube, K-2041 (Bioneer, Alameda, Calif.), which contains a lyophilized mixture of RTase enzyme, dNTP, RNase inhibitor, reaction buffer, tacking dye and patented stabilizers. The tube contents were left at room temperature for 1 minute, then vortexed, briefly spun, and 28 µL of the contents were transferred to the chamber of the device.

2-3. Device Loading

The microfluidic device of Example 2-1 was prepared for operation as follows. The analysis channel network was filled with a separation gel comprising 200 mM TAPS buffer at pH 8 and 3% polydimethylacrylamide matrix. First, 15 µL of separation gel was added to well 1, and positive pressure over well 1 was used to introduce the gel into the channel network. 15 µL of separation gel was then added to each of wells 3, 4, and 9. Next, 15 a of focusing dye was added to well 2, and then 15 µL of DNA marker solution was added to well 8. The PCR reaction solution (28 µL) of Example 2-2 was added to the chamber via well 5. After the chamber was completely filled, 15 µL of separation gel buffer was added to well 7, and light pressure was applied over well 7 for 10 seconds. Finally, 15 µL of 20 cst silicone oil was added to wells 5 and 6 (inlets to the reaction chamber) and well 7.

The distribution of reagents is summarized in the table, and below that the solution components are listed.

| | Well # | | | | | | |
|---|---|---|---|---|---|---|---|
| | 2 | 1 | 3 | 4 | 7 | 8 | 9 | Chamber |
| Solution | Focusing dye | Gel | Gel | Gel | PCR buffer | DNA Markers | Gel | PCR reaction solution |

Focusing Dye: 0.2 µM 5-carboxytetramethylrhodamine (TAMRA) in gel buffer

Gel Buffer: 3 mM MgCl$_2$, 200 mM TAPS, pH 8.0

Gel: 3% PDMA31-146 in gel buffer

PCR Buffer: 1×KOD buffer, 3 mM MgCl$_2$, 200 mM TAPS (pH 8.0), 0.2% Proclin 300

DNA Markers: TAMRA-labeled 300 and 500 base pair dsDNA (1 ng/µL each) in gel buffer The loaded microfluidic device was mounted on the thermal cycling device as described in Example 1-3.

2-4. Device Operation

Real-time RTPCR-CE analysis of the loaded microfluidic device prepared by Example 2-3 was performed as follows.

The reverse transcriptase (RT) reaction was performed by incubating the microfluidic device at 42° C. for 20 min.

The PCR thermocycling protocol was conducted with the following sequence of denaturing, annealing, and extension temperatures and times:

Cycles 1-14: 101° C. for 7 s, 60° C. for 14 s, and 74° C. for 8 s.

Cycles 15-40: 101° C. for 7 s, 62° C. for 14 s, and 77° C. for 39 s.

After the first 14 cycles were performed, beginning with cycle 15, sample components of the PCR reaction solution were removed from the chamber by electrophoresis after each PCR cycle, moved to the separation channel and analyzed by electrophoresis. The potential or the current at the electrode in each well was controlled according to the following protocol:

| Step | Time [sec] | Well2 | Well1 | Well3 | Well4 | Well7 | Well 8 | Well9 |
|---|---|---|---|---|---|---|---|---|
| First | 10 | 0.2 uA | -2.2 uA | 1700 V | -2 uA | -15 uA | -5 uA | 0 uA |
| Second | 21 | 0.2 uA | 1500 V | | 2 uA | 500 V | -15 uA | -5 uA | 22 uA |
| Third | 29 | 0.2 uA | 1500 V | | 2 uA | 500 V | 0 uA | 0 uA | 2 uA |

The first, second, and third steps correspond to the application of a first voltage, second voltage, and third voltage as illustrated in FIGS. 3A-3C. The protocol was initiated 29 seconds after the start of PCR cycle 15. The first step of potential and current control was applied for 10 seconds, the second step conditions were applied for 21 seconds, and the third step conditions were applied for 29 seconds, and then the same protocol of potential and current control for the first, second, and third steps was repeated through to the end of the PCR reaction.

2-5. Results

In conducting the PCR and electrophoretic protocol described in Example 2-4, samples of the reaction product were withdrawn after each cycle beginning with cycle 15 and subjected to capillary electrophoresis (CE) analysis.

Figure 10A:
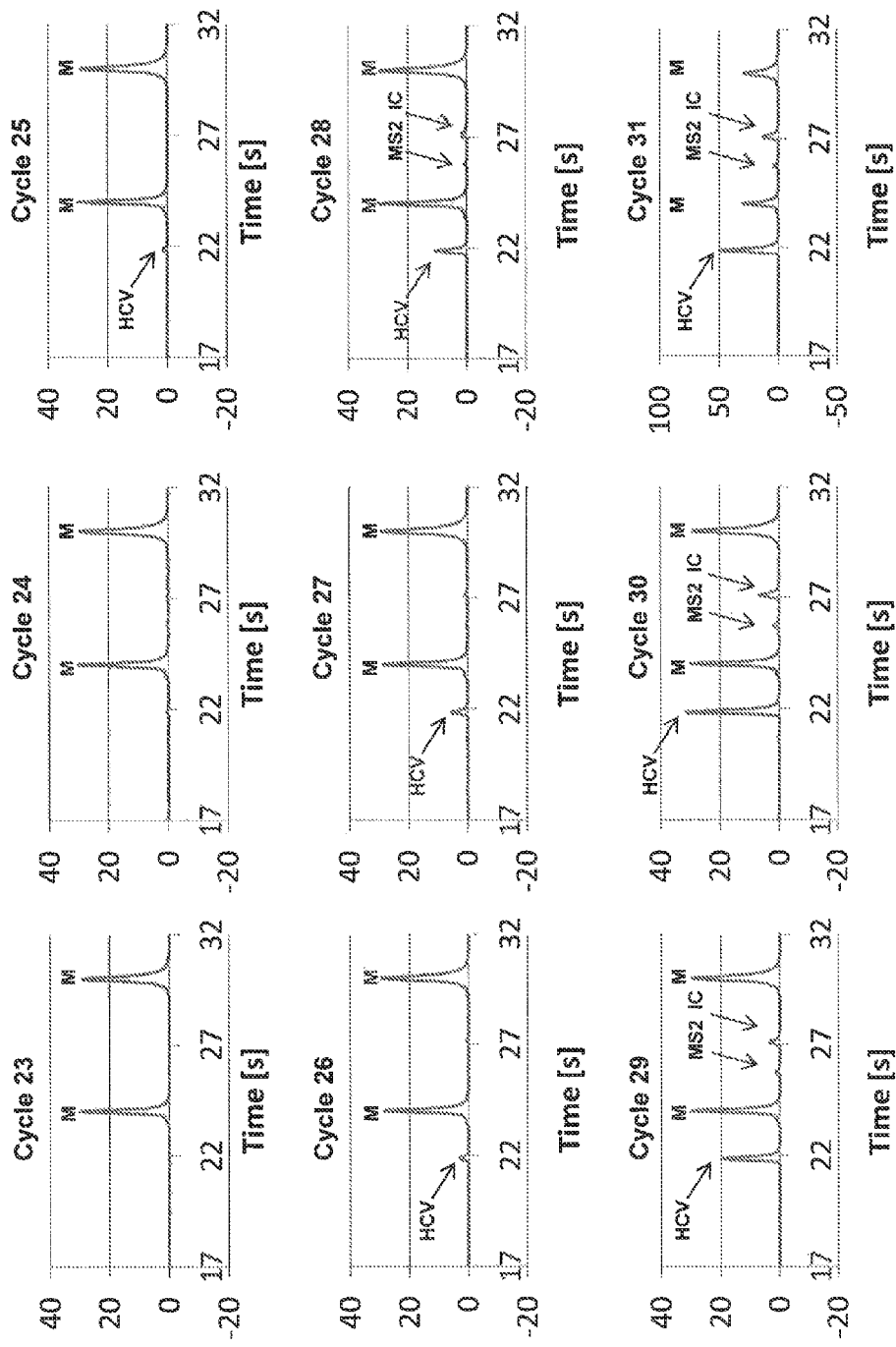
FIGS. 10A and 10B show the results of a real-time RT-PCR-CE analysis conducted according to one embodiment of the invention described in Example 2.

By conducting the PCR and electrophoretic protocol described in Example 2-4, samples of the reaction product were withdrawn after each cycle beginning with cycle 15 and subjected to capillary electrophoresis analysis. The electropherograms analyzing the products produced by cycle 23, 24, 25, 26, 27, 38, 29, 30 and 31 are shown in FIG. 10A (from left to right, top row to bottom row). In the electropherogram analyzing the products of cycle 23, at the upper left, the two marker peaks are readily apparent. The two peaks are, respectively, 300, and 500 base pair markers. The expected amplicon (100 base pairs) peak is indicated by the arrow. The expected HCV amplicon peak is just perceptible in the upper right electropherogram (produced in cycle 25). The MS2 and internal control (IC) peaks are apparent starting from cycle 28.

The growth of the peaks for the HCV target, the MS2 control, and PCR internal control demonstrated that RNA was extracted from the viral particles, RNA was converted by RT to DNA, the DNA was amplified by PCR, and the amplicon products were withdrawn from the reaction chamber, transported to the separation channel, and successfully analyzed by CE.

Figure 10B:
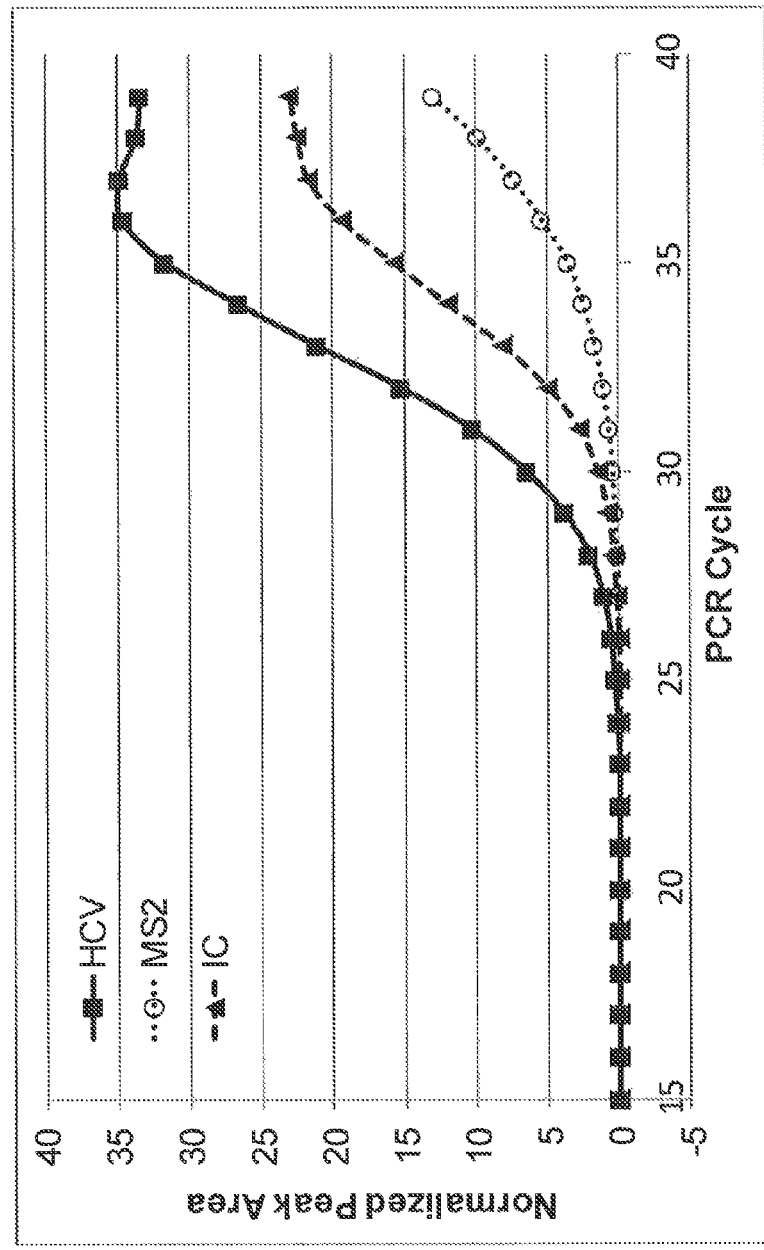

FIG. 10B shows the growth curve of the product and two controls, that is, the amount of amplicon as a function of cycle number, for the same experiment. As seen in FIG. 10B, the cycle number (Cq) at which the amount of amplicon crosses a threshold of 2 was 28.0 for HCV, 30.6 for PCR internal control and 33.6 for MS2.

Example 3: PCR Reaction with Sampling Every Other Cycle 3-1. Device

The device described in Example 1-1 was used.

3-2. PCR Reaction Solution

Primers for amplifying a 200 base region of bacteriophage-λ genome were synthesized with the following sequences and used to prepare a PCR reaction solution. The reverse primer was labeled with a fluorescent dye, 5-carboxytetramethylrhodamine (TAMRA).

Phage-λ primers:

```
                            SEQ ID NO: 7
(forward primer)  5'- CGGGATAACACGCTCACCATGA SEQ ID NO: 8
(reverse primer)  5'-TAMRA-GGCCAGACCGAGCCTTCAATAC
```

PCR reaction solutions were prepared with the following composition: 1×PCR buffer (see below), 0.4 mM dNTP, 0.05 U/μL KOD exo(−) polymerase, 0.2% Procline 300 (Supelco, 48912-U), 1% CHAPS (Dojindo Laboratories, C-008), 0.1% Olfine (Nissin, AK-02), 0.2 μM forward primer, 0.2 μM reverse primer. Lambda Phage DNA obtained from Sigma-Aldrich (Product No. D9768) was added as the template at a concentration of 10,000 copies/25 μL of reaction solution.

3-3. Device Loading

The microfluidic device of Example 3-1 was prepared for operation as follows. The analysis channel network was filled with a separation gel comprising 200 mM TAPS buffer at pH 8 and 3% polydimethylacrylamide sieving matrix as described in Example 2-3. The PCR reaction solution (25 μL) of Example 3-2 was loaded into access well 6 and delivered to chamber 11 by capillary action. Well 7 was filled with PCR buffer. Silicone oil (15 μL; 20 cst) was added to wells 5 and 6 (inlets to the reaction chamber) and well 7. Other wells were filled with separation gel or markers or focusing dye as indicated by the distribution of reagents is shown in the table below.

|  | Well # | | | | | | | |
|---|---|---|---|---|---|---|---|---|
|  | 2 | 1 | 3 | 4 | 7 | 8 | 9 | Chamber |
| Solution | Focusing dye | Gel | Gel | Gel | PCR buffer | DNA Markers | Gel | PCR reaction solution |

Focusing Dye: 0.2 μM 5-carboxytetramethylrhodamine (TAMRA) in gel buffer

Gel Buffer: 3 mM MgCl$_2$, 200 mM TAPS, pH 8.0

Gel: 3% PDMA31-146 in gel buffer

PCR Buffer: 1×KOD buffer, 3 mM MgCl$_2$, 200 mM TAPS (pH 8.0), 0.2% Proclin 300

DNA Markers: TAMRA-labeled 300 and 500 base pair dsDNA (1 ng/μl each) in gel buffer The loaded microfluidic device was mounted on the thermal cycling device as described in Example 1-3, 3-4. Device Operation Real-time PCR-CE analysis of the loaded microfluidic device prepared by Example 3-3 was performed as follows. PCR thermocycling protocol was programmed with the following sequence of denaturing, annealing, and extension temperatures and times:

Cycle 1: 104° C. for 120 s, 63.8° C. for 14 s, and 74.5° C. for 8 s.

Cycle 2-16: 101° C. for 7 s, 63.8° C. for 14 s, and 74.5° C. for 8 s.

Cycle 17: 101° C. for 7 s, 63.8° C. for 14 s, and 74.5° C. for 59 s.

Repeat the following to the end of the assay:

Cycle 18 (even): 101° C. for 7 s, 63.8° C. for 14 s, and 74.5° C. for 39 s.

Cycle 19 (odd): 101° C. for 7 s, 63.8° C. for 14 s, and 74.5° C. for 8 s.

First, 17 cycles were performed. Then, beginning with cycles 18 and 19, sample components of the PCR reaction solution were removed from the chamber by electrophoresis 29 sec after each even numbered PCR cycle (the first cycle in the pair of cycles, e.g., cycle 18, 20, etc.), moved to the separation channel and analyzed by electrophoresis. The timing diagram is reflected by FIG. 4C. The potential or the current at the electrode in each well was controlled according to the following protocol:

| Step | Time [sec] | Well2 | Well1 | Well3 | Well4 | Well7 | Well 8 | Well9 |
|---|---|---|---|---|---|---|---|---|
| First | 10 | 0.2 uA | −2.2 uA | 1700 V | −2 uA | −15 uA | −5 uA | 0 uA |
| Second | 21 | 0.2 uA | 1500 V | | 2 uA | 500 V | −15 uA | −5 uA | 22 uA |
| Third | 29 | 0.2 uA | 1500 V | | 2 uA | 500 V | 0 uA | 0 uA | 2 uA |

The first, second, and third steps correspond to the application of a first voltage, second voltage, and third voltage as illustrated in FIGS. 3A-3C. The protocol was initiated 29 seconds after the start of PCR cycle 18. The first step of potential and current control was applied for 10 seconds, the second step conditions were applied for 21 seconds, and the third step conditions were applied for 29 seconds, and then the same protocol of potential and current control for the first, second, and third steps was repeated through to the end of the PCR reaction.

3-5. Results

Figure 11B:
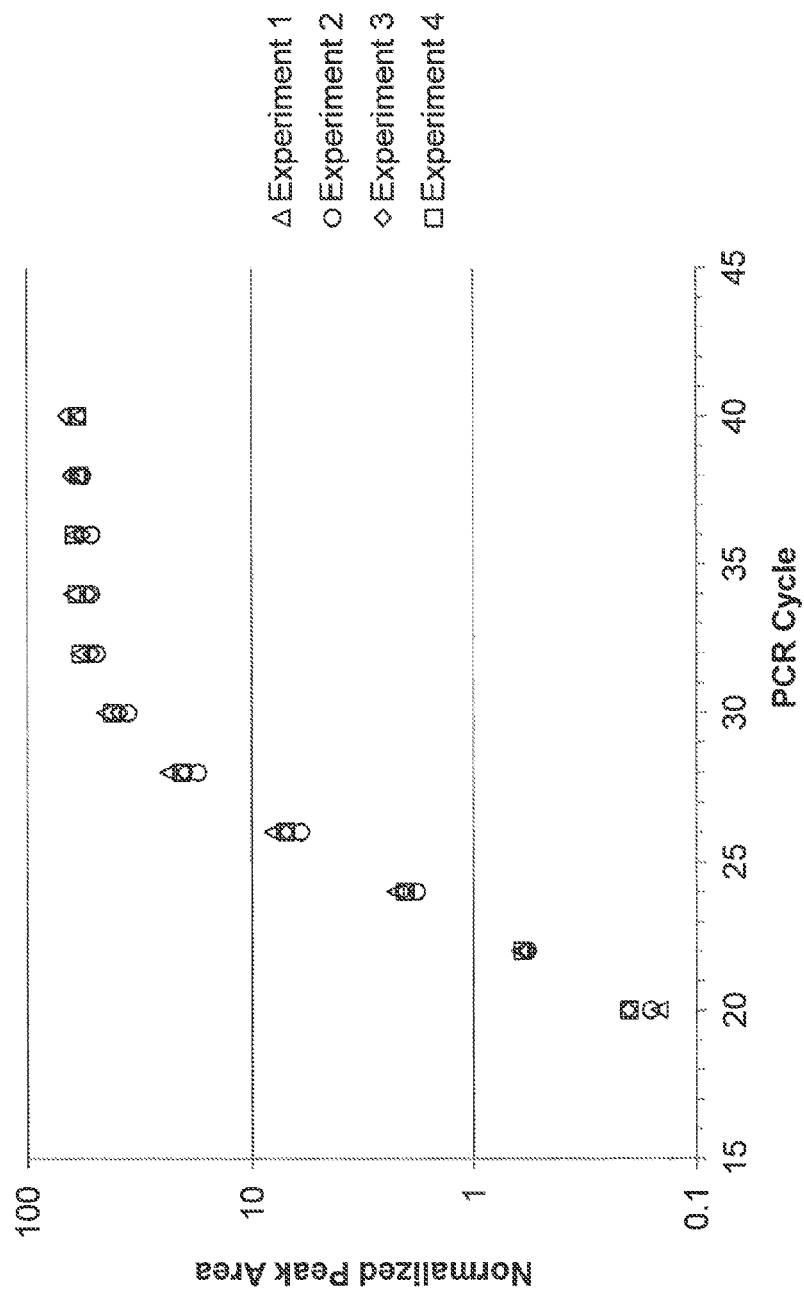

By conducting the PCR and electrophoretic protocol described in Example 3-4, samples of the reaction product were withdrawn after even cycle numbers beginning with cycle 18, and analyzed by capillary electrophoresis in the microfluidic device. The series of electropherograms analyzing the products of cycle 18, 20, 22, 24, 26, 28, 30, 32, and 34 are shown in FIG. 11A. In the electropherograms, the DNA marker peaks are readily apparent at about 25 s (300 bp marker) and 30 s (500 bp marker). The peak at about 15 s is the primers, and the 200 bp target amplicon (indicated by the arrow) appears at about 22 s. The expected amplicon peak is just perceptible in the upper middle electropherogram (products of cycle 20), and dominates the electropherogram in the last electropherogram shown (products of cycle 34). FIG. 11B shows the growth curve of the amount of target amplicon as a function of PCR cycle number, from four replicate experiments, and demonstrates the reproducibility of the method.

Although the invention has been described with respect to particular embodiments and applications, those skilled in the art will appreciate the range of applications and methods of the invention disclosed herein.

We claim:

1. A method for analyzing sample components in a microfluidic device comprising a chamber, a load channel that leads from the chamber to a load waste well, a separation channel that leads from a separation head well to a separation waste well and intersects the load channel, and a preload channel that leads from the load channel at a position between the chamber and the load channel/separation channel intersection to a preload waste well, wherein:
the length of the load channel from the chamber to load channel/separation channel intersection is distance A, the length of the load channel from the load channel/preload channel junction to the load channel/separation channel intersection is distance B, and distance A and distance B satisfy the following conditions:
(1) $v_{fast}(T_1) <$ distance A;
(2) $v_{slow}(2 \cdot T_1 + T_2) >$ distance A;
(3) $v_{slow}(T_1) >$ distance B;
wherein $v_{fast}$ is the electrokinetic velocity of the fastest component of interest in the sample, and $v_{slow}$ is the electrokinetic velocity of the slowest component of interest in the sample;
the method comprising the steps of:
(a) adding an assay solution to the chamber;
(b) applying a first voltage across the chamber and the load waste well for a first length of time $T_1$ to move (i) a first set of sample components from the assay solution at a first time and previously moved into the load channel into a load channel/separation channel intersection region and (ii) a second set of sample components removed from the assay solution at a second time from the chamber into the load channel;
(c) subsequent to step (b), applying a second voltage across the chamber and the preload waste well for a second length of time $T_2$ to continue to move the second set of sample components removed from the assay solution at a second time from the chamber and in the load channel towards the preload waste well; and
(d) subsequent to step (b), applying a third voltage across the separation head well and separation waste well for a third length of time $T_3$ to inject the first set of sample components from the load channel/separation channel intersection region into the separation channel and to perform an analysis of the first set of sample components in the separation channel.

2. The method according to claim 1, wherein the distance A is 0.1-2 cm.

3. The method according to claim 2, wherein the distance A is 0.3-0.8 cm.

4. The method according to claim 1, wherein the distance B is 0.01-0.2 cm.

5. The method according to claim 1, wherein steps (c) and (d) at least partially overlap in time.

6. The method according to claim 5, wherein step (c) begins when step (b) ends.

7. The method according to claim 6, wherein step (d) begins when step (b) ends.

8. The method according to claim 5, wherein step (b) is repeated after step (d) ends.

9. The method according to claim 8, wherein the cycle of steps (b), (c), and (d) is repeated at least 10 times.

10. The method according to claim 1, wherein the sample components move by electrophoresis.

11. The method according to claim 1, further comprising performing at least one nucleic acid amplification reaction in the chamber after step (a).

12. The method according to claim 11, wherein the following series of steps (b)-(e) is repeated at least twice:
   step (b);
   step (c);
   step (d); and
   (e) performing at least one amplification cycle beginning at the end of step (c);
wherein:
   the first time the series of steps is performed, step (d) is optionally omitted;
   the subsequent series of steps begins after step (d) and step (e) end; and
   optionally, the last time the series of steps is repeated, the series of steps only includes step (b) and step (d).

13. The method according to claim 12, wherein:
   steps (c) and (d) begin when each step (b) ends; and
   one amplification cycle is performed in each step (e), which begins at the end of each step (c).

14. The method according to claim 1, wherein the sample components comprise at least one polynucleotide.

\* \* \* \* \*